United States Patent
Garside et al.

(10) Patent No.: US 6,411,373 B1
(45) Date of Patent: Jun. 25, 2002

(54) FIBER OPTIC ILLUMINATION AND DETECTION PATTERNS, SHAPES, AND LOCATIONS FOR USE IN SPECTROSCOPIC ANALYSIS

(75) Inventors: Jeffrey J. Garside; Stephen Monfre, both of Gilbert; Barry C. Elliott, Phoenix; Timothy L. Ruchti, Gilbert; Glenn Aaron Kees, Tempe; Frank S. Grochocki, Phoenix, all of AZ (US)

(73) Assignee: Instrumentation Metrics, Inc., Chandler, AZ (US)

( * ) Notice: Subject to any disclaimer, the term of this patent is extended or adjusted under 35 U.S.C. 154(b) by 0 days.

(21) Appl. No.: 09/415,389

(22) Filed: Oct. 8, 1999

(51) Int. Cl.$^7$ .............................. G01N 33/48; G02B 6/04
(52) U.S. Cl. ......................................... 356/39; 385/115
(58) Field of Search ................................. 385/115, 116, 385/123, 120, 121; 356/39, 301; 600/310, 182

(56) References Cited

U.S. PATENT DOCUMENTS

| | | | |
|---|---|---|---|
| 5,551,422 A | 9/1996 | Simonsen et al. | 128/633 |
| 5,635,402 A | 6/1997 | Alfano et al. | 436/63 |
| 5,813,403 A | 9/1998 | Soller et al. | 128/633 |
| 5,830,132 A | 11/1998 | Robinson | 600/310 |
| 5,953,477 A | 9/1999 | Wach et al. | 385/115 |
| 6,006,001 A | * 12/1999 | Alfano et al. | 385/115 |

FOREIGN PATENT DOCUMENTS

| | | | |
|---|---|---|---|
| EP | 0 494 734 A2 | 7/1992 | 21/35 |
| EP | 0843986 | 5/1998 | A61B/5/00 |
| WO | WO 97/27800 | 8/1997 | |
| WO | WO 98/30889 | 7/1998 | 21/47 |
| WO | WO 99/09455 | 2/1999 | |

OTHER PUBLICATIONS

Jacques, *Tissue Optics– Short Course Notes*, SPIE's Photonics West, 1997, SPIE—The International Society for Optical Engineering.

Hannemann et al., *Neonatal Serum Bilirubin from Skin Reflectance*, School of Medical Engineering, Purdue University, 1978.

Jagemann et al., *Application of Near–Infrared Spectroscopy for non–invasive determination of Blood/Tissue Glucose using Neural Networks*, Zeitschrift fur Physikalische Chemie, Bd. 191, 1995.

(List continued on next page.)

*Primary Examiner*—Frank G. Font
*Assistant Examiner*—Layla Lauchman
(74) *Attorney, Agent, or Firm*—Michael A. Glenn; Christopher Peil

(57) ABSTRACT

The invention provides a design process that is used in the determination of the pattern of detector and illumination optical fibers at the sampling area of a subject. Information about the system, specifically a monochromator (e.g. to determine the optimal number of fibers at an output slit) and the bundle termination at a detector optics stack (e.g. to determine the optimal number of fibers at the bundle termination), is of critical importance to this design. It is those numbers that determine the ratio and number of illumination to detection fibers, significantly limiting and constraining the solution space. Additional information about the estimated signal and noise in the skin is necessary to maximize the signal-to-noise ratio in the wavelength range of interest. Constraining the fibers to a hexagonal perimeter and prescribing a hex-packed pattern, such that alternating columns contain illumination and detection fibers, yields optimal results. In the preferred embodiment of the invention, two detectors share the totality of the detection fibers at the sampling interface. A third group of detection fibers is used for classification purposes.

30 Claims, 23 Drawing Sheets

OTHER PUBLICATIONS

Heise, *Medical Application of Infrared Spectroscopy*, Mikrochim, Acta, Springer–Verlag, 1997.

Janatsch et al., *Mulitvariate Calibration for Assays in Clinical Chemistry Using Attenuated Total Reflectance Infrared Spectra of Human Blood Plasma*, Anal: Chem, 1989.

Marquardt et al., *Near–Infrared Spectroscopic Measurement of Glucose in a Protein Matrix*, Anal: Chem 1993.

Wilson et al, Optical reflectance and transmittance of tissues: Principles and Applications, Dec. 1990, *IEEE Journal of Quantum Electronics*.

Robinson et al, Noninvasive Glucose Monitoring in Diabetic Patients: *A Preliminary Evaluation*, 1992, Clin. Chem.

Hazen, *Glucose Determination in Biological Matrices Using Near–Infrared Spectroscopy*, Aug. 1995, University of Iowa.

* cited by examiner

FIBER OPTIC ILLUMINATION AND DETECTION PATTERNS, SHAPES, AND LOCATIONS FOR USE IN SPECTROSCOPIC ANALYSIS

BACKGROUND OF THE INVENTION

1. Technical Field

The invention relates to the use of fiber optics for the illumination of analyte samples and for the detection of signals present at such analyte samples. More particularly, the invention relates to fiber optic illumination and detection patterns, shapes, and locations for use in the noninvasive global-estimation of analytes, such as blood glucose.

2. Description of the Prior Art

To those knowledgeable in the art, the size, arrangement, and number of detection and illumination optical fibers at the interface of a probe designed to launch and collect light from a tissue sample, such as human skin, significantly impacts the received signal.

Various attempts have been made in the past to provide devices that illuminate and collect light from a tissue sample. See, for example, K. Maruo, K. Shimizu, M. Oka, Device For Non-Invasive Determination of Glucose Concentration in Blood, European Patent Application No. EP 0 843 986.

However, such known devices have provided less than satisfactory results. It would be advantageous to provide a method and apparatus for optimizing fiber optic illumination and detection patterns, shapes, and locations for use in the noninvasive prediction of analytes, such as blood glucose.

SUMMARY OF THE INVENTION

The invention provides a method and apparatus for optimizing fiber optic illumination and detection patterns, shapes, and locations for use in the noninvasive prediction of analytes, such as blood glucose. If the optical system is appropriately modeled, the received signal can be predicted. By systematically exploring patterns, shapes, and fiber locations, the invention herein disclosed makes it possible to optimize the optical system design by maximizing desirable quantities in a system model, for example the signal-to-noise ratio (SNR).

In the example of the signal-to-noise ratio, the signal is directly related to the photon pathlength in the subject's dermis and the noise is approximately inversely proportional to the intensity as a function of wavelength and detector to illumination fiber separation distance. Additionally, the number of fibers at a monochromator output slit and at the bundle termination at a detector optics stack can be determined, causing the optimization to become particularly constrained. Once this constraint is in place, it becomes significantly easier for the pattern of illumination and detection fibers to be investigated and optimized. Finally, the shape of the perimeter of the fiber layout is dictated by simple geometrical considerations.

Throughout this process, fabrication constraints should be ignored whenever possible. Only after arriving at an optimal solution can tradeoffs concerning tolerable losses for the sake of practicality and expediency be properly addressed.

DETAILED DESCRIPTION OF THE INVENTION

Figure 1:
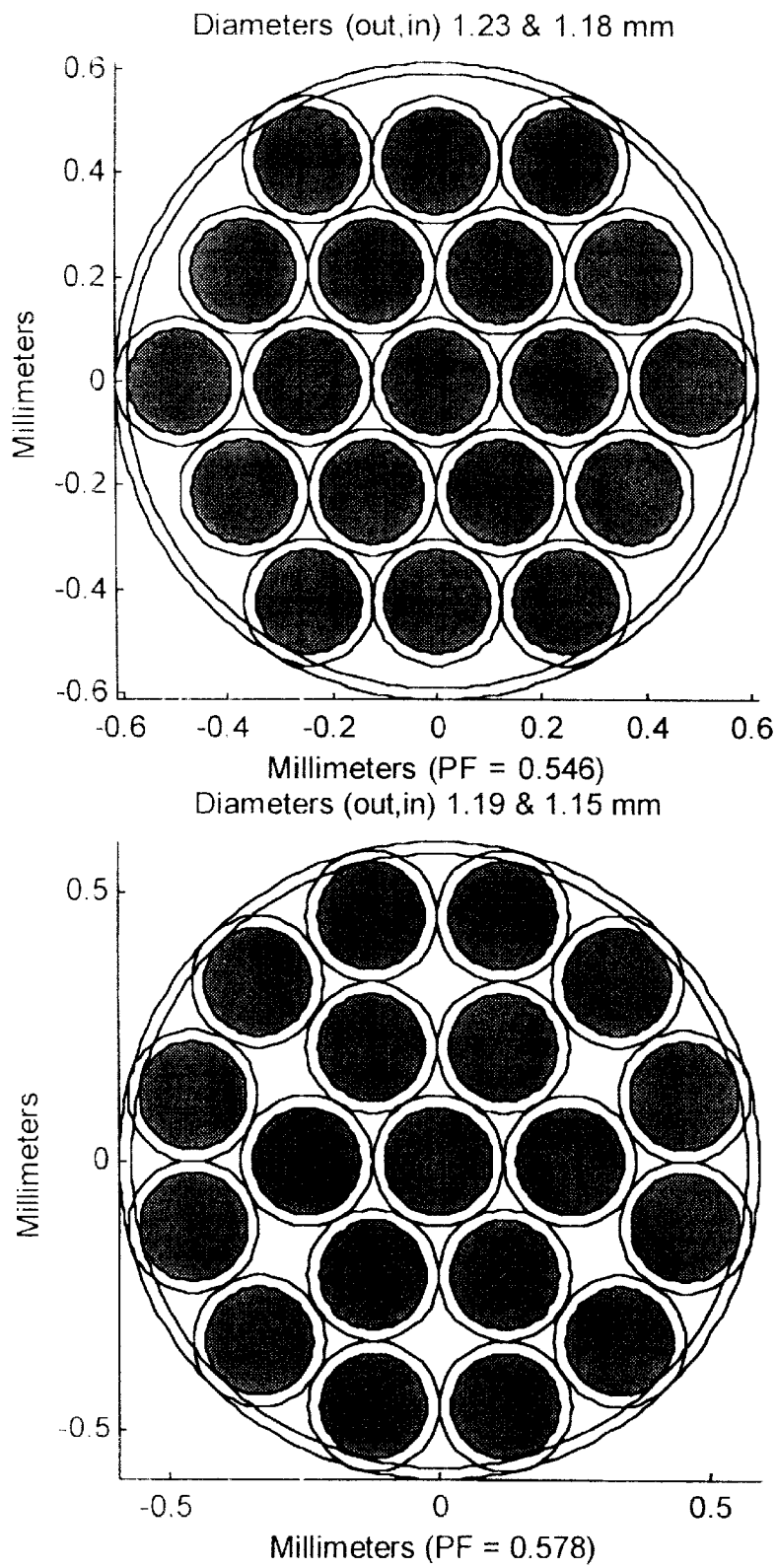
FIG. 1 is a schematic diagram illustrating a nineteen fiber circular layout, where concentric rings of fibers are seen to be beneficial, in terms of overall diameter of the bundle, in comparison to a hex pack according to the invention.

The invention is directed to the development of an optimized fiber probe geometry for use in the area of diffuse reflectance and diffuse transmission spectroscopy. While the preferred embodiment of the invention is concerned with noninvasive measurements, other applications of the invention include measurements of moisture, fat, and protein in agricultural products, e.g. sugar in fruit or protein in cereal; reaction monitoring of slurry solutions; textile manufacturing; polymer melts, pellets, and additives; polymer tensile strength; active ingredients of pharmaceutical tablets; and active ingredients of gel caplets, to name a few. Such applications can be performed either during a QC/QA analysis, or they may be applied to real time process control.

The invention provides a process for designing fiber optic bundles in specific patterns and shapes and distances (between illumination and detection fibers). Initially, the design is constrained to the use of specific fiber types and detector size, thereby simplifying the optimization process significantly (see Table 1 below). The invention provides a fiber optic bundle that includes both illumination and detection fibers. In the preferred embodiment of the invention, the detection and illumination fibers have the same characteristics, wherein said fiber characteristics comprise any of type, size, numeric aperture, and core-to-clad ratio.

TABLE 1

Preferred Fiber Types

| Fiber | Specific Type | Numerical Aperture (NA) | Size (Core/Clad) |
|---|---|---|---|
| Illumination | UltraSil 200T* | 0.22 | 200/240 µm |
| Detection | TCL-MA200H* | 0.29 | 200/220 µm |

\* Available from SpecTran Specialty Optics of Avon, Conn. Note that the buffer layer should be removed from the fiber ends in the preferred embodiment of the invention.

The monochromator used in the preferred embodiment of the invention is the Minichrome Monochromator manufactured by Optometrics of Ayer, Mass. Finally, the preferred detector size is prescribed to be 1 mm in diameter. These design decisions should be made prior to the commencement of any modeling attempts or the application of an optimization scheme, as described herein.

Several pieces of information can be derived from the above mentioned design decisions. The first of these includes a curve that estimates the intensity at the output slit of the monochromator. The second is a function that approximates the efficiency of focusing the light from the detector fiber bundle through a long wave pass filter, two lenses, and a window, onto the detector itself.

The signal of interest (which, in exemplary embodiment of the invention, is the absorbance attributable to glucose) is assumed to be proportional to the ratio of pathlength of the average photon in the dermis of the subject's skin to its total pathlength, i.e. the photon distribution along a mean path. A tissue model was developed and a Monte Carlo simulation (see below) run to estimate the average pathlength that the photon traveled, as well as what fraction of that pathlength was in the subject's dermis.

The noise is approximated using a noise model (see below), after some mathematical simplifications, of the intensity of the sample (e.g. the subject's arm). These data were generated from a wide area radial fiber (WARF) probe (described below). A function is then empirically fitted to the data. This function is used to generate the necessary representation of noise.

All of this information is incorporated into a single program that uses a graphical user interface to allow for an interactive design and analysis of an arbitrary fiber layout. Designs are saved and used as input into a genetic algorithm that selects the best designs and attempts to improve upon them. The best pattern is then modified slightly (which usually leads to marginal incremental improvements) to yield a regular pattern throughout and to fit into the external geometry selected (in this case a hexagon or a rectangle).

Finally, a third fiber optic field for detection is included in the design because it significantly improves subject classification (see, for example, S. Malin, T. Ruchti, An Intelligent System for Noninvasive Blood Analyte Prediction, U.S. patent application Ser. No. 09/359,191, filed Jul. 22, 1999), which is believed to be an important precursor to algorithm application.

Detailed Description

Optimization

Generally, it is desirable to design for the best or optimal solution, indicating the lack of ability to improve upon a design. In the presence of design constraints, however, the term optimal solution is often employed meaning the best solution, given the tradeoffs and practical considerations. The term optimization, as used herein, means the maximization of a cost or evaluation function in some manner based upon a pre-defined set of mathematical operations. With regard to the preferred embodiment of the invention described herein, the evaluation function is an estimate of the modeled signal-to-noise ratio. The optimization criterion maximizes the sum of this evaluation function in a portion of the combination band (2100–2250 nm) that is deemed to be representative of the glucose molecule's absorption in that region.

Weights & Penalties

Detector Penalty

As discussed above, light from the detector fibers is focused onto the detector using a two lens system. The detector fiber bundle is preferably the same shape as the detector (i.e. circular) to maximize the amount of light leaving the detector fibers that strikes the detector. Consequently, the optimal arrangement of the detector fibers at the lens is circular. As the number of detector fibers increases, both the amount of space these fibers occupy and the radius of the fiber bundle increase. The fibers at the perimeter of the fiber bundle contribute less light to the detector than the fibers at the center of the bundle. Additionally, because the image of the fiber bundle is constrained to the size of the detector and the magnification is finite, optical radiation is collected less efficiently with an increased bundle size. This effect can be quantified using a Zemax™ Raytrace model (manufactured by Focus Software, Inc. of Tucson, Ariz.) to provide an overall efficiency of light delivered to the detector as a function of the fiber bundle radius, once the location and specifications for the lenses and any other elements in the optical paths are established. The efficiency can then be considered as a detector radius penalty that allows for optimization of the detector fiber bundle.

To use this information, it is necessary to determine the detector fiber bundle radius for a given number of fibers. For the purpose of simulation, it is assumed that the fibers are placed in a manner that minimizes the fiber bundle radius. The best alternative for this minimization is to place the fibers in concentric rings. While it may intuitively seem that a hex pack configuration is more effective than a concentric ring configuration, a theoretical arrangement having nineteen fibers illustrates that this is not the case (see FIG. 1).

Figure 2:
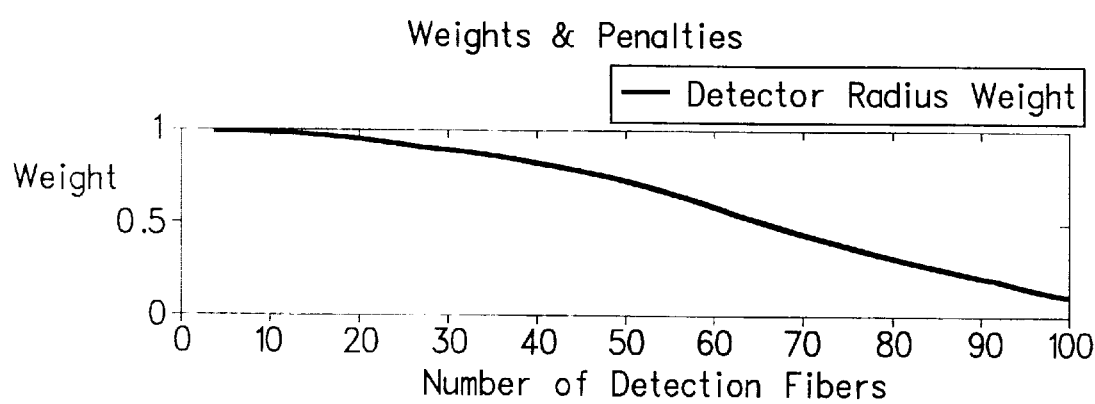
FIG. 2 is a plot of the penalty associated with an increased number of fibers at a detector.
Figure 3:
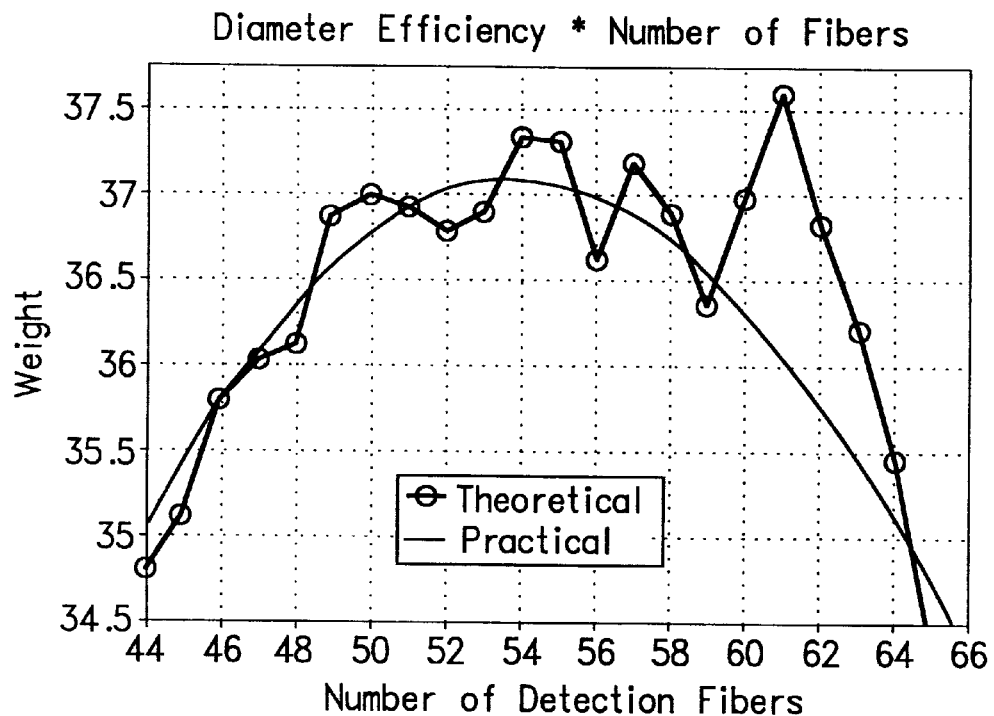
FIG. 3 is a plot of diameter efficiency multiplied by the number of fibers as a function of the number of fibers, illustrating trade-off between illumination gain from increased detectors and loss from the associated lower efficiency.

The actual cost function associated with fiber bundle radius is to best determine the optimal number of detector fibers. By examining FIG. 2, the loss of light efficiency as the number of fibers increases can be seen. Counteracting this loss of efficiency is the increased amount of light delivered by the larger number of fibers. FIG. 3 illustrates the region of interest used to determine the optimal tradeoff between increasing the number of fibers and detector optical design efficiency. Initially, as the number of detection fibers increases, the weight function increases. However, at a point around 54 fibers, the extra light from adding additional fibers is overshadowed by the increased loss in efficiency. Therefore, nothing is gained by adding further fibers.

In can be noted from FIG. 3 that the theoretical curve of this interaction is not smooth. This is a result of a change in the theoretical fiber packing fraction at the detector bundle termination. Adding an incremental number of fibers does not increase the diameter of the fiber bundle linearly. In fact, in going from sixty to sixty-one fibers, the bundle diameter does not increase at all. As the theoretical best packing fraction is not attainable in manufacturing, it is deemed best to use the practical function shown in FIG. 3.

Note that detector fibers are preferably positioned with a bundle center fiber at the detector being likewise centered at the fiber bundle interface at the subject's dermis so that the center fiber is at the center at each end of the bundle. This arrangement is preferably applied to each and every fiber in the bundle, e.g. outermost fibers are outermost at each end.

Monochromator Penalties

The output slit of the monochromator is rectangular resulting in a rectangular best shape for the monochromator fiber bundle. This suggests to one skilled in the art the use of a hexagonal packing arrangement to maximize the packing fraction, which in turn maximizes the amount of light collected from the monochromator.

The optical dimensions of the monochromator help to determine the optimal size of the monochromator fiber bundle. To obtain the desired resolution from the monochromator, the height for the monochromator slit should be less than 1 mm. With this in mind, the number of rows is immediately set. Given the number of rows in the fiber bundle, the optical slit height can be determined according to the following equation:

$$\text{Optical Slit Height} = (\text{\# Rows} - 1) * \frac{\sqrt{3}}{2} * \text{Fiber Diameter} + \text{Core Diameter} \tag{1}$$

Finally, if the total number of illumination fibers is known, the number of fibers in each row as well as the width of the fiber bundle can be calculated.

Note that illumination fibers are preferably positioned with a bundle center fiber at the monochromater slit being likewise centered at the fiber bundle interface with the subject (the subject's dermis is an inner portion of skin tissue, hence the fiber bundle interface does not occur at the dermis) so that the center fiber is at the center at each end of the bundle. This arrangement is preferably applied to each and every fiber in the bundle, e.g. outermost fibers are outermost at each end.

Figure 4:
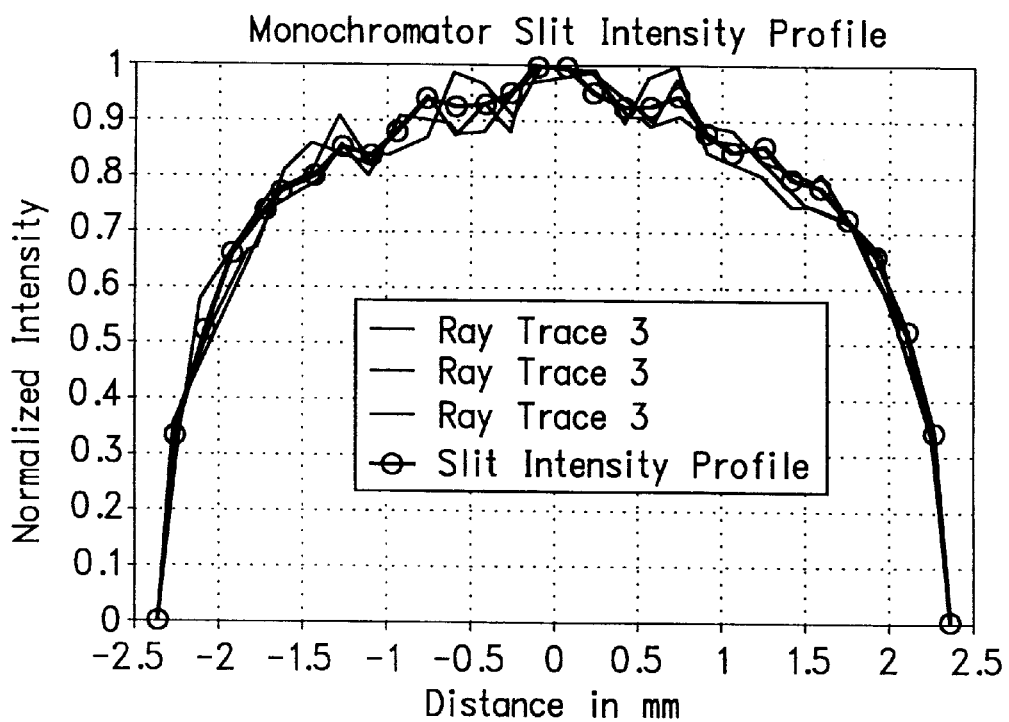
FIG. 4 is a plot of a monochromator output slit intensity illustrating the loss associated from fibers located horizontally off-center in the monochromator output slit.
Figures 5, 6:
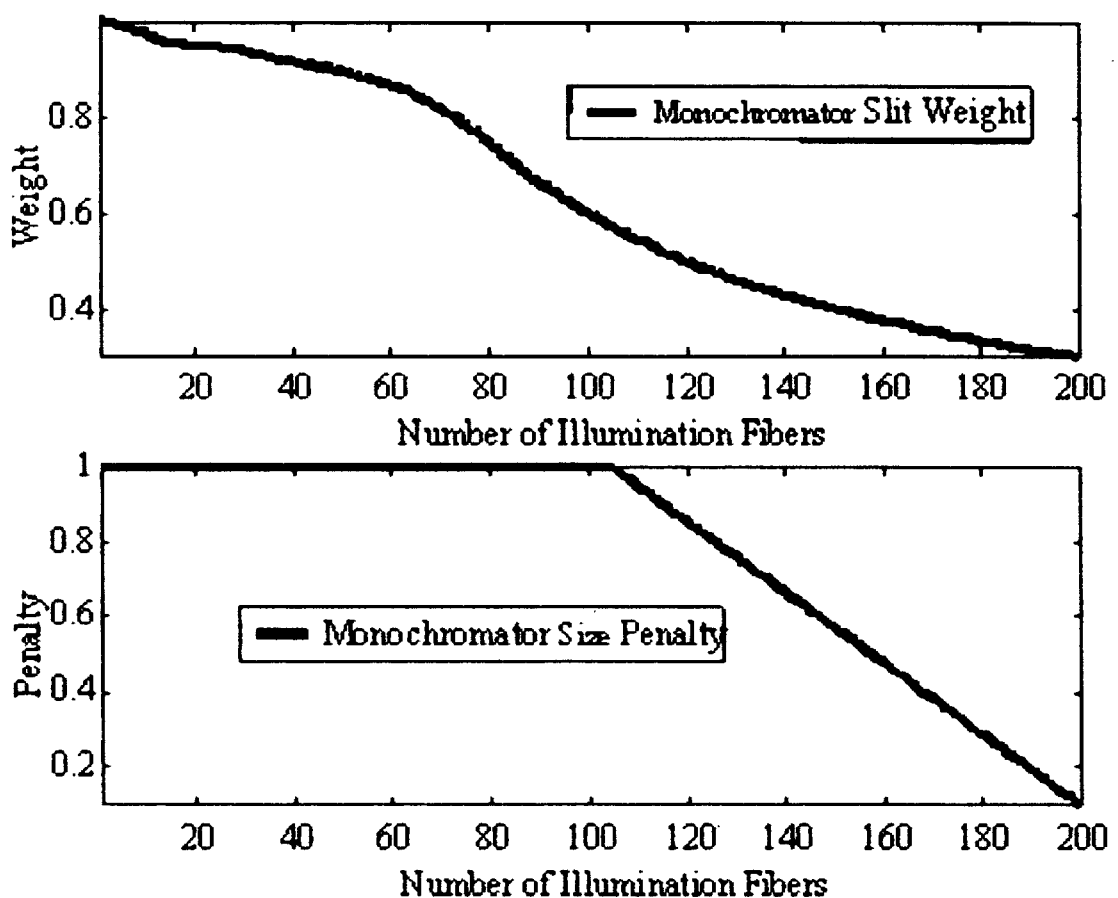
FIG. 5 is a plot of the penalty associated with increased number of fibers at the monochromator.
FIG. 6 is a plot of an additional penalty to keep fibers from being placed at the monochromator without receiving any light.

Fibers in the bundle that are further from the center collect and distribute less light to the skin surface. This effect can be quantified using an Opticad® Raytrace Model (manufactured by Opticad Corp. of Santa Fe, N.Mex.). FIG. 4 illustrates the results of three such raytrace simulations and their average used in the simulations. Assuming, for the sake of simplicity, a uniform distribution of fibers at the monochromator output slit, the average intensity in each illumination fiber can be computed. The value of the raytrace results is averaged (over the computed monochromator slit height) to obtain a scale factor for the entire monochromator fiber bundle (see FIG. 5). This scale factor is a number between 0 and 1 that represents what fraction of the maximum intensity (which is defined to be 1.0 at the center of the monochromator output slit) each illumination fiber is assumed to carry.

It can be seen from FIG. 4 that a fiber offset by more than 2.4 millimeters horizontally from the center of the monochromator output slit contributes no light. The method described above does not penalize this scenario sufficiently. Doubling the number of fibers halves the light (recall these are all tested average fibers) and the simulation delivers light to the sample through fibers which receives no light. Therefore, an additional monochromator size penalty is included which further penalizes the scenarios where the size of the monochromator slit height is greater than 4.8 millimeters (see FIG. 6). For the fiber size being proposed and the monochromator size, the breakpoint in the penalty function occurs at 105 fibers. If more fibers are added, they deliver no light to the sample.

Scaling Factors

Data for estimating the noise is obtained using the WARF probe with a first type of fibers F1, e.g. 300/330/370 $\mu$m (i.e. core/clad/buffer). To use this data to simulate other sizes of fibers, certain scaling factors must be taken into consideration. The amount of light delivered to the skin is proportional to the area of the illumination fiber. Similarly, the amount of light collected at the skin is proportional to the area of the detector fiber. The scale factor for fiber area is then:

$$SF = \left(\frac{\text{Diameter of } F2 \text{ Detector Core}}{\text{Diameter of } F1 \text{ Detector Core}}\right)^2 \times \qquad (2)$$

$$\left(\frac{\text{Diameter of } F2 \text{ Illumination Core}}{\text{Diameter of } F1 \text{ Illumination Core}}\right)^2$$

Where F2 is a second type of fiber, e.g. 200/220 µm, 200/240 µm (i.e. core/clad).

The numerical aperture (NA) of all F1 fibers is 0.22. For the illumination fibers proposed, the NA is also 0.22. No scale factor is necessary. For the detector fibers, a NA of 0.29 is chosen to maximize the amount of light collected. A scale factor equal to the square of the NA ratios is used:

$$SF = \left(\frac{\text{NA of } F2 \text{ Detector Fiber}}{\text{NA of } F1 \text{ Detector Fiber}}\right)^2 \qquad (3)$$

The data collected with the WARF probe considers the effect of one fiber placed in the center of a ring of six fibers. Depending on whether the one center fiber is a collection or illumination fiber (and the six fibers are illumination and collection fibers, respectively), intensity variations arise due to inefficiencies in the detector optics. For the simulations, it is desired to determine what effect one illumination fiber has on one detection fiber when completely focused on the detector. To do this, a comparison between the above-described cases is made and a scale factor of 1.475 is determined to be the appropriate scale factor.

Signal

The signal of interest, in this instance the absorbance due to glucose, is assumed (via Beer's Law) to be proportional to the pathlength of the light as it travels through the dermis, referred to as $L_{Dermis}$. Additionally, because glucose is located predominantly in the vascularized portion of the dermis, the glucose signal is better represented by the fraction of the pathlength in the dermis when divided by the overall pathlength ($L_{Dermis}/L_{Total}$). In a medium in which intensity does not diminish with fiber separation distance, the best scenario for detecting the glucose signal is the one received with a maximum $L_{Dermis}/L_{Total}$ term. For that case, whatever fiber optic pattern that yields a maximum for that term is preferential to all others, although other signal definitions are possible.

Figure 7:
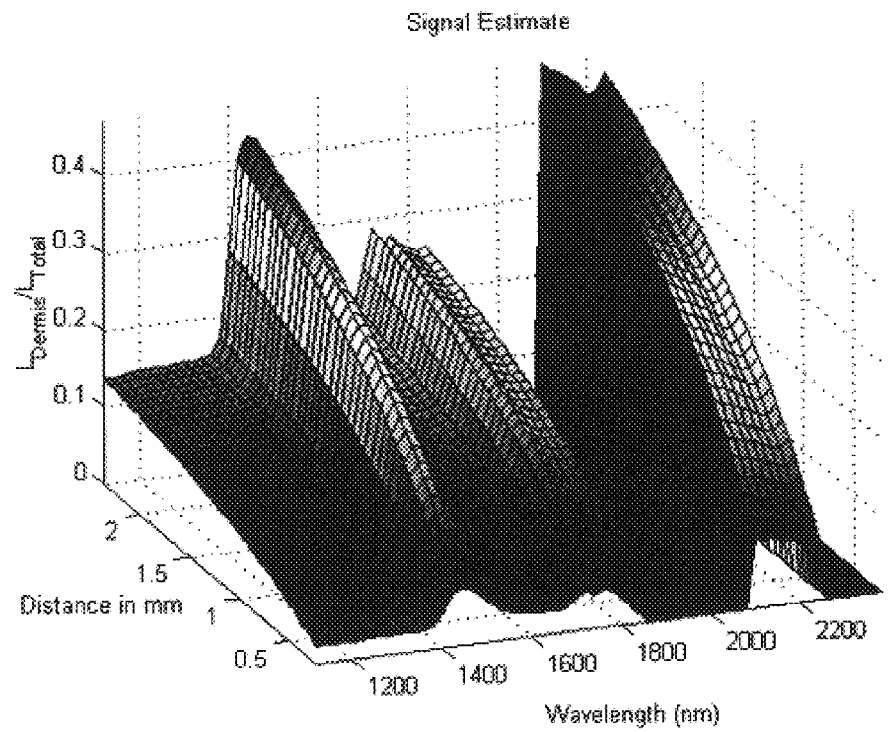
FIG. 7 is a plot of an estimate of a signal using Monte Carlo simulations according to the invention.

This information is determined for the wavelength region of interest, as well as for a variety of fiber separation distances (illumination to detection fiber separation distances). It serves as the signal in computing the SNR. The data were compiled and curve fitted for ease of representation and computation (see FIG. 7).

Noise

Noise (in absorbance units) in the system is typically represented by:

$$Noise = 0.4343 \sqrt{\frac{N_R^2}{I_R^2} + \frac{N_S^2}{I_S^2}} \qquad (4)$$

where $N_R$ and $N_S$ are the noise in the reference and sample intensity measurements, respectively, and $I_R$ and $I_S$ are the intensities in the reference and sample, respectively. This simplifies (given several assumptions) to a value that is proportional to $1/I_S$ in the instance where the system is dominated by sample noise (which is the case). A function representing the sample intensity as a function of distance (separation between fibers) and wavelength adequately models the noise.

Such a data set exists: the Wide Angle Radial Fiber (WARF) probe results. The resulting function is expressed as:

$$1/\text{Noise } e^{(a_\lambda + b_\lambda \sqrt{d})} \qquad (5)$$

where $a_\lambda$ and $b_\lambda$ are empirically derived parameters for each wavelength, and d is the fiber separation distance.

Figure 8:
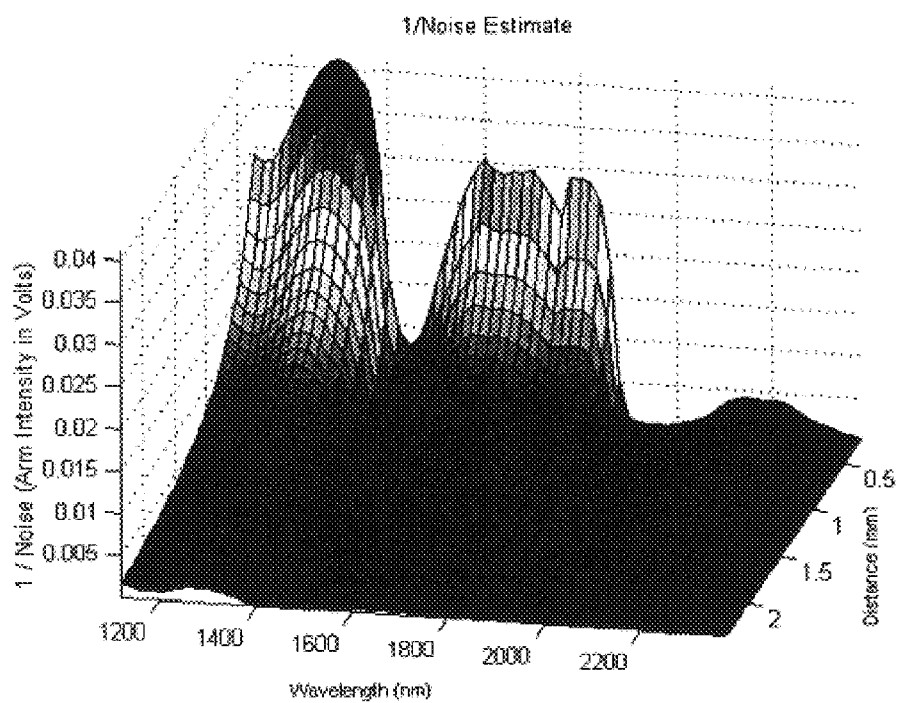
FIG. 8 is a plot of an estimate of the function 1/Noise using a wide area radial fiber (WARF) probe according to the invention.

The contribution of the WARF probe results to the overall cost function is that it estimates the noise portion of the signal-to-noise ratio. Data on the WARF probe exists across the wavelength ranges of interest, as well as at varying distances (separation of illumination and detection fibers). A description of that system is beyond the scope of the discussion herein. The data were compiled and curve fitted for ease of representation and computation (see FIG. 8).

Algorithm for Evaluation

To evaluate a potential fiber layout, the above-described quantities are combined into an evaluation function. This evaluation function takes into consideration the separation in fiber distances, the SNR (signal-to-noise ratio), and the various aspects of the monochromator output slit and detector optics stack. In its functional form, the evaluation function, which itself is a function of wavelength, is computed for the $i^{th}$ detector as follows:

$$EF_i(\lambda) = \sum_{Illum} \sum_{Detec_i} S(\lambda, d) * \frac{1}{N(\lambda, d)} * DP(\# Detec_i) * \qquad (6)$$

$$MP(\# Illum) * MSP(\# Illum) * SF(Type, Size)$$

where $EF_i$ is the evaluation function for the $i^{th}$ detector; the signal, S, and noise, N, are functions of wavelength, λ, and illumination to detection fiber separation distance d; DP is the detector penalty as a function of the number of detection fibers; MP is the monochromator penalty as a function of the number of illumination fibers; MSP is the monochromator size penalty as a function of the number of illumination fibers; and SF is a scaling factor that is a function of fiber sizes and types.

Figure 9:
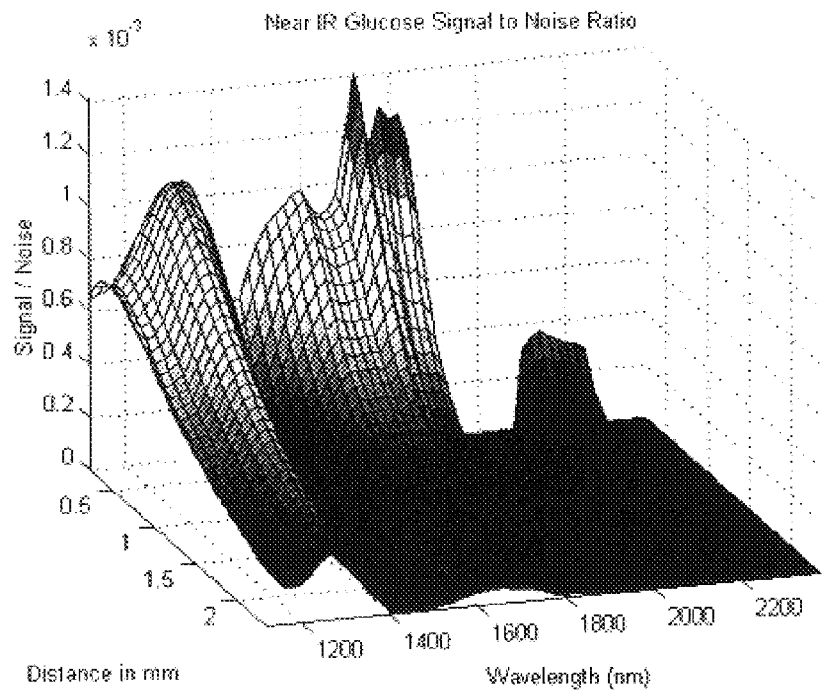
FIG. 9 is a three-dimensional plot of a near-IR (NIR) glucose signal-to-noise ratio as a function of wavelength and separation distance of illumination source and detector according to the invention.
Figure 10:
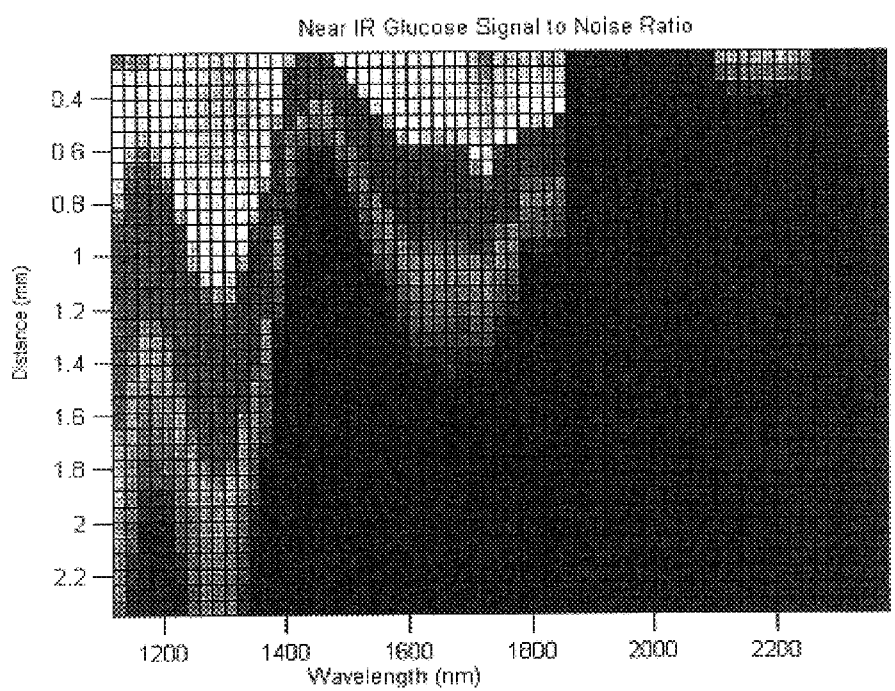
FIG. 10 is a plot of an alternate view of an NIR glucose signal-to-noise ratio illustrating the peaks near the lowest separation distance according to the invention.

The actual function is difficult to evaluate, but computational steps can be avoided by doing the following:

1) Noting that the signal/noise ratio is the same for similar fiber separation distances. Thus, S/N ratio can be computed for each unique distance and then multiplied by the number of detector/illumination fiber pairs at that distance (see FIGS. 9 and 10).

2) DP*MP*MSP*SF do not need to be computed inside the summation.

3) Signal and noise only need to be computed once for each unique distance and then can be saved in memory for later use. This avoids extremely time consumptive re-computation.

4) Pre-computing the distances between all fibers and using a look-up table to determine the separation distance between any two specific fibers.

Note, if only the signal term is set to 1.0 because noise is proportional to intensity of an arm scan, the evaluation function predicts the intensity off of an arm scan. This allows for model validation on a F1 fiber probe or on any custom bundle that is designed.

Optimization

Figure 11:
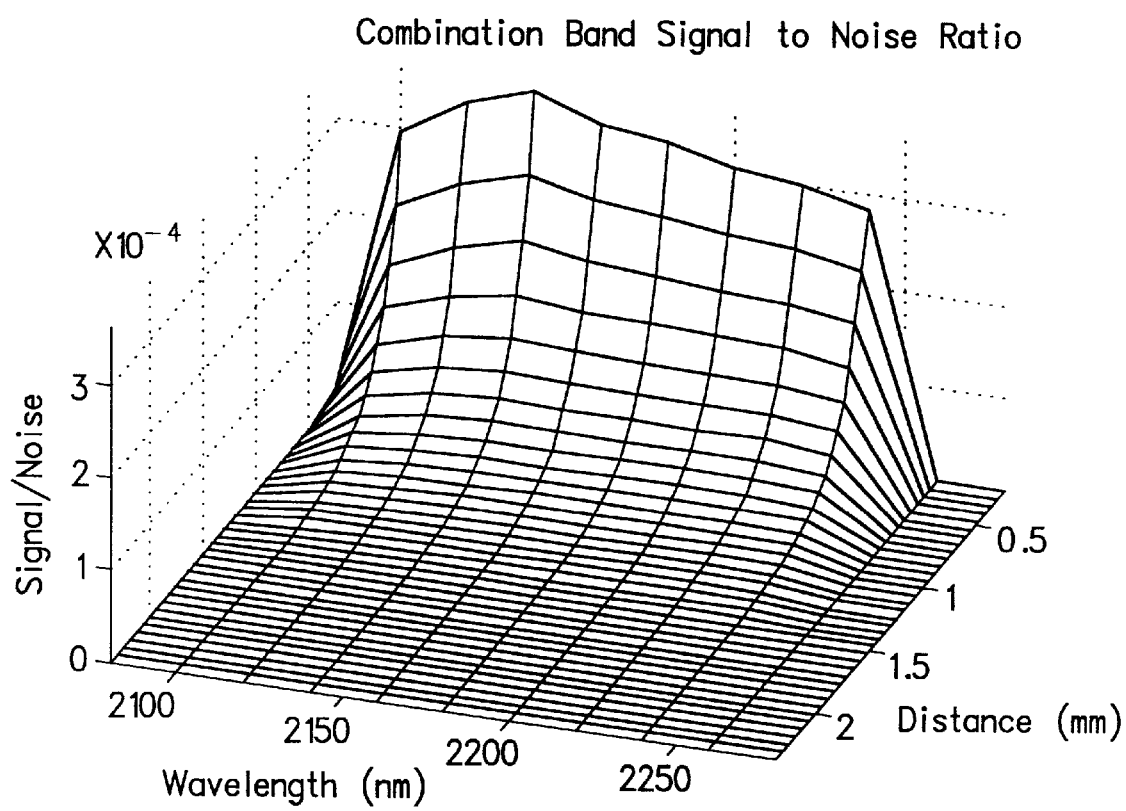
FIG. 11 is a plot showing magnification of an NIR glucose signal-to-noise ratio in the combination band according to the invention.

The evaluation function is used to compare and contrast designs. For example, the decision is made to optimize this design for the maximum signal-to-noise ratio in the combination band (see FIG. 11). As a result, the optimization becomes:

$$BestDesign_i = \max\left(\sum_{\lambda=2100nm}^{2250nm} EF_i(\lambda)\right) \quad (7)$$

That is, the best design for a given detection fiber is the one that maximizes the evaluation function for that detector over the wavelength range of interest, here 2100–2250 nm.

To discover what pattern yields the best results, hundreds of initialization patterns were investigated. Each of these patterns is used as input to a genetic algorithm that keeps the best patterns and tries to improve upon them. After a certain amount of effort, the genetic algorithm is discontinued and the best results are examined. Usually, those results are intelligently modified to yield slightly better results.

Figure 12:
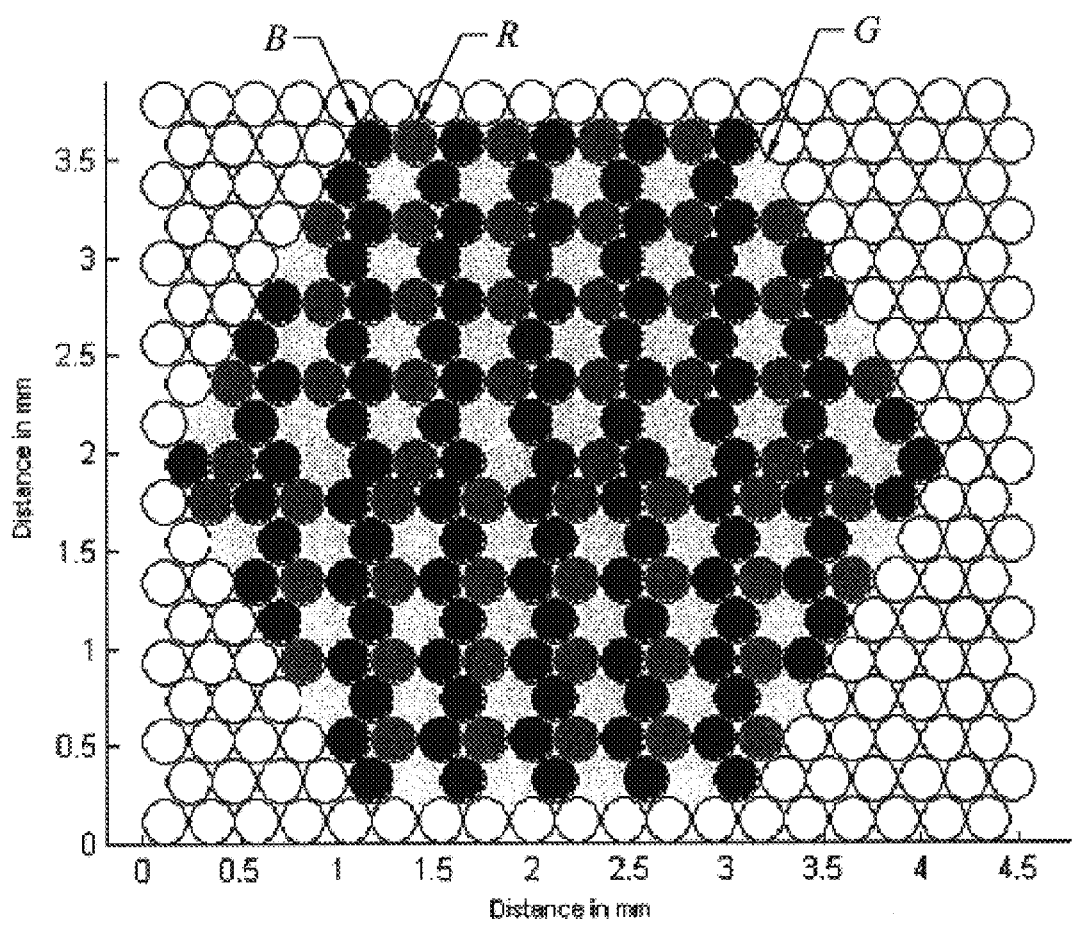
FIG. 12 is a schematic diagram illustrating a hexagonal fiber optic interface according to the invention.

The genetic algorithm produces a result similar to that displayed in FIG. 12. Black circles B represent illumination fibers and the gray circles R and G are 1.9 $\mu$m and 2.6 $\mu$m detection fibers. The basic pattern comprises alternating columns of illumination and detection fibers.

Perimeter

Figure 13:
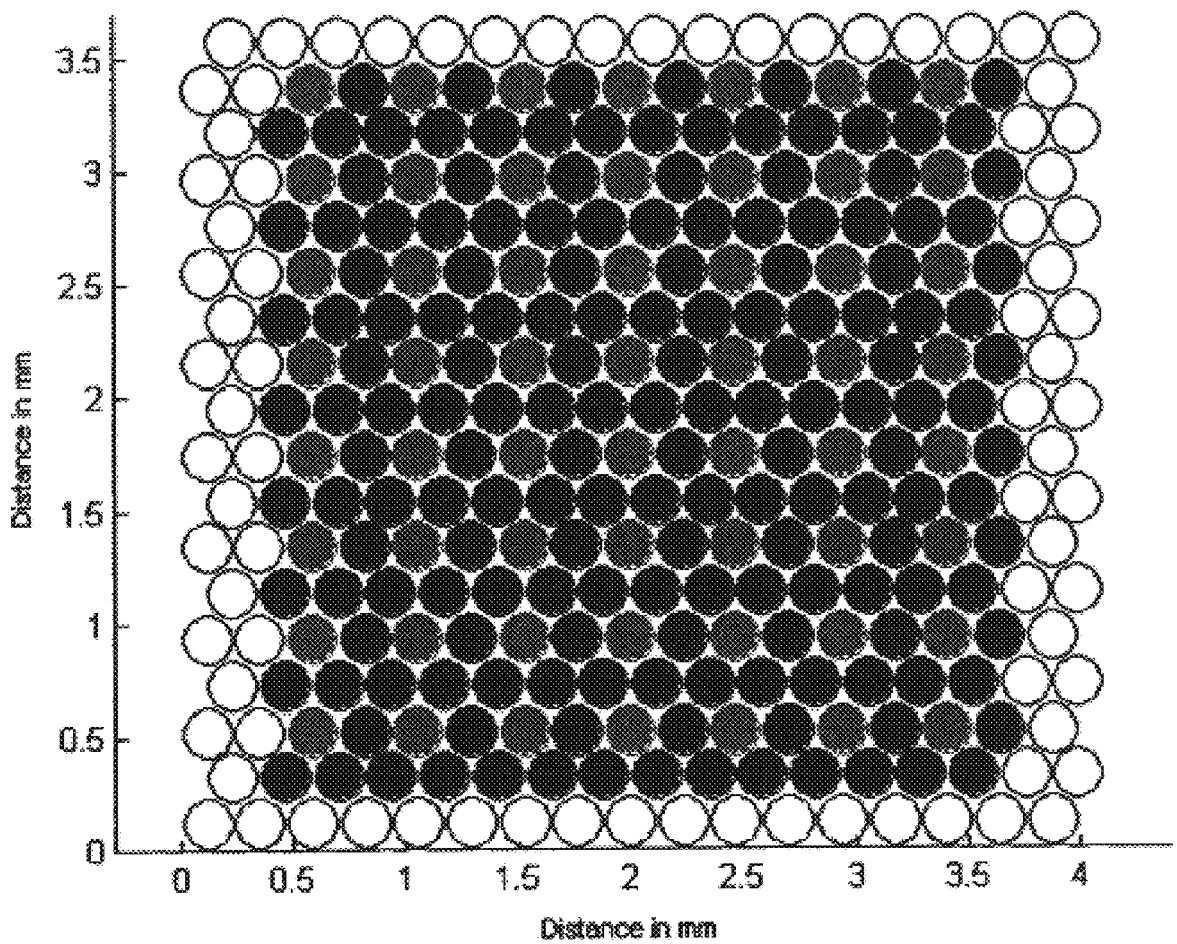
FIG. 13 is a schematic diagram illustrating a square fiber-optic interface according to the invention.

The perimeter displayed is approximately a square (see FIG. 13). However, if it is feasible to build a fiber bundle having a hexagonal perimeter, there is a gain in the net signal.

Figure 14:
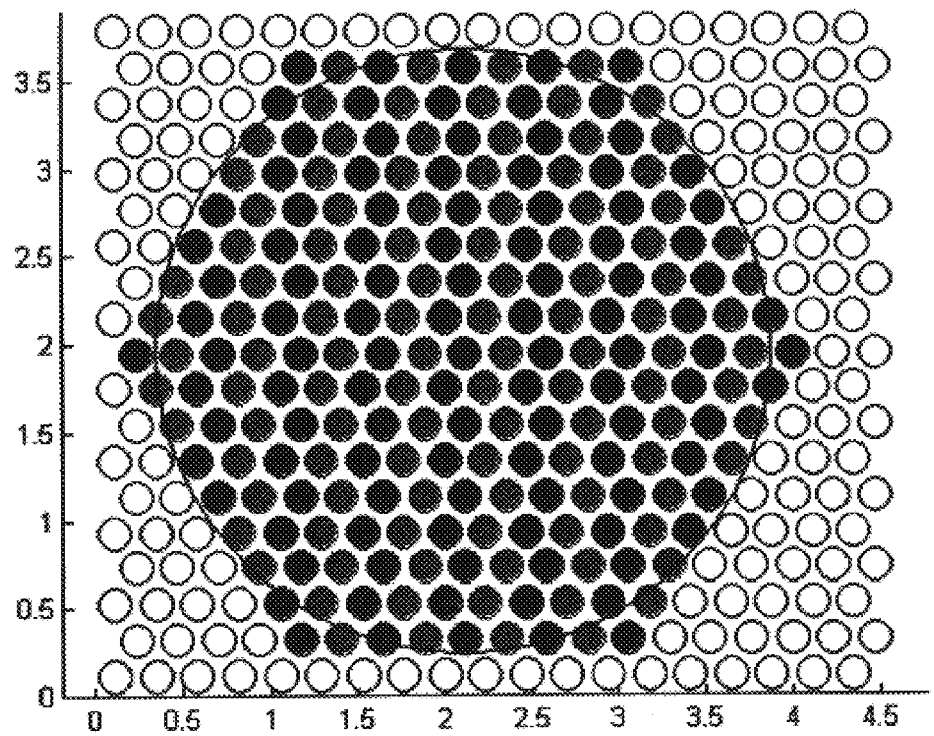
FIG. 14 is a schematic diagram illustrating a hexagonal arrangement with a circle superimposed showing how close a hexagon represents a circle for a hex pack according to the invention.
Figure 15:
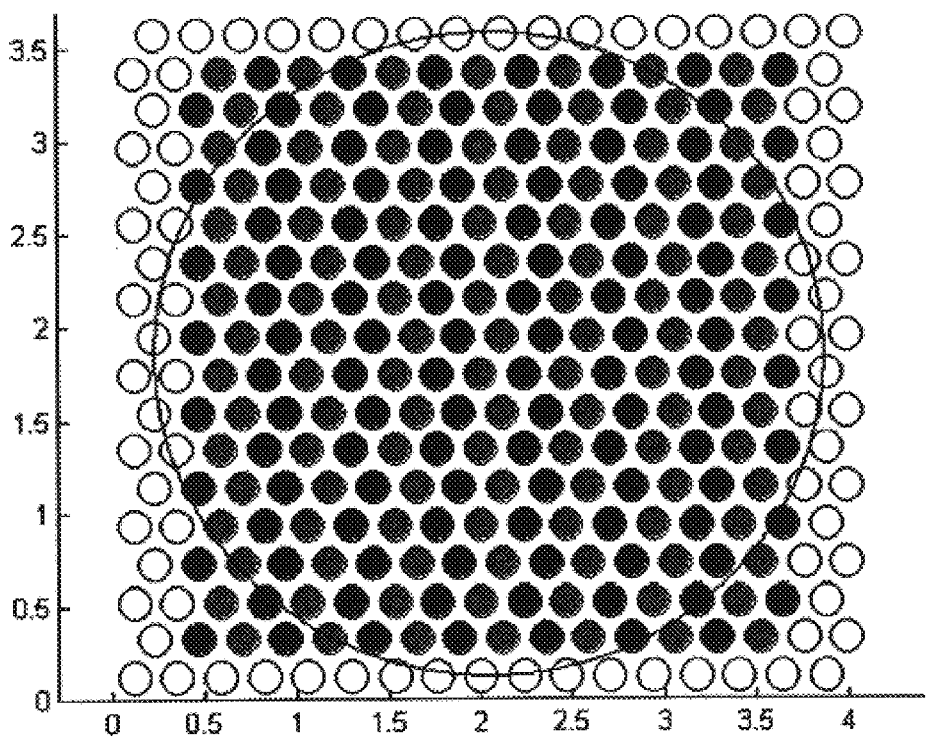
FIG. 15 is a schematic diagram illustrating a square arrangement with a circle superimposed demonstrating slight losses associated with a square configuration versus a hexagon configuration according to the invention.

Ideally, the perimeter is a circle. The closest approximation to a circle with hex-packed fibers is a hexagon, as shown in FIG. 14. A square is also feasible, coming within about 5% of the predicted results given by a hexagon. Compare the plot of FIG. 14 which is for a hexagon configuration with the plot of FIG. 15 which is for a square configuration. Both plots have circles superimposed on them to show how close these perimeters are to the ideal case.

Final Design

Figure 16:
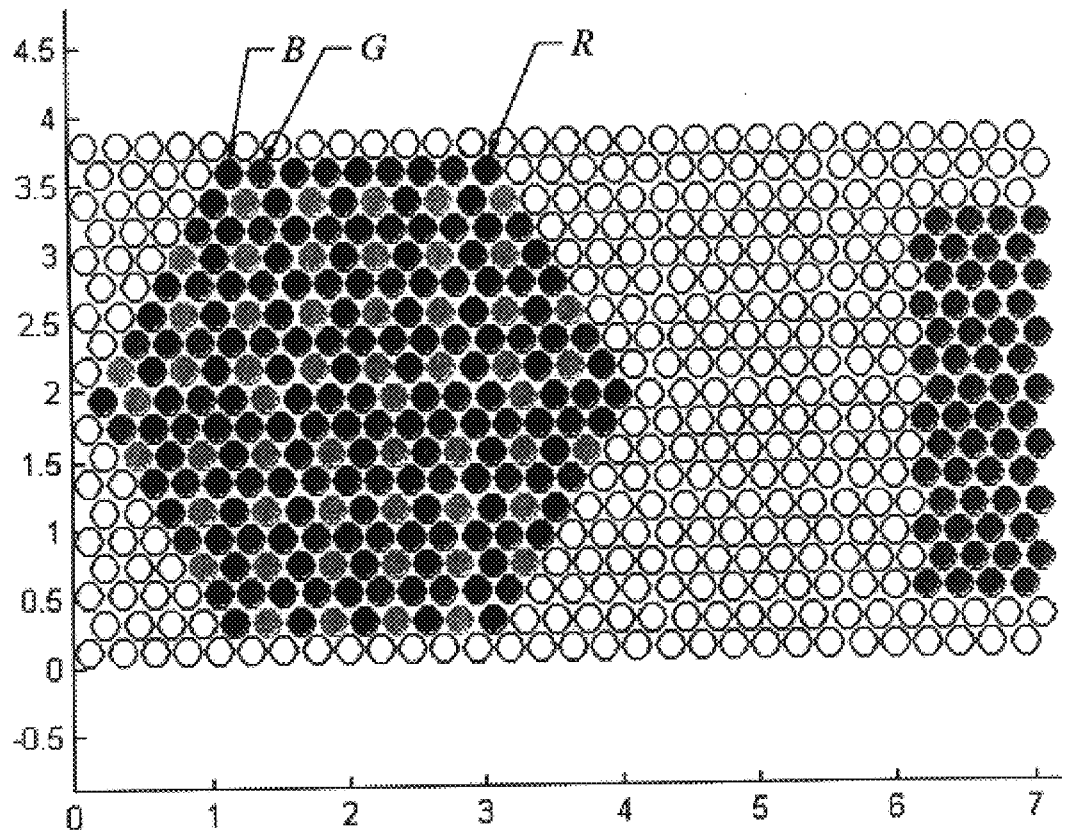
FIG. 16 is a schematic diagram illustrating a hexagonal skin interface with a classification detector according to the invention.
Figure 17:
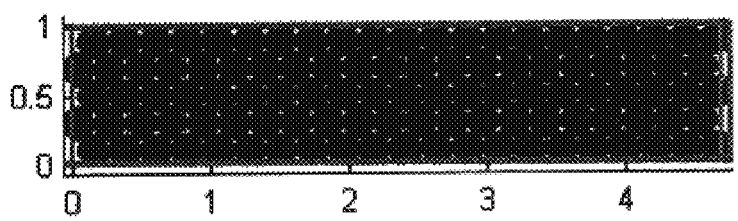
FIG. 17 is a schematic diagram illustrating a 200/220 $\mu$m (core/clad) fiber optic pattern at a monochromator output slit, where a configuration of 105 fibers is shown (i.e. the exact amount), according to the invention.
Figure 18:
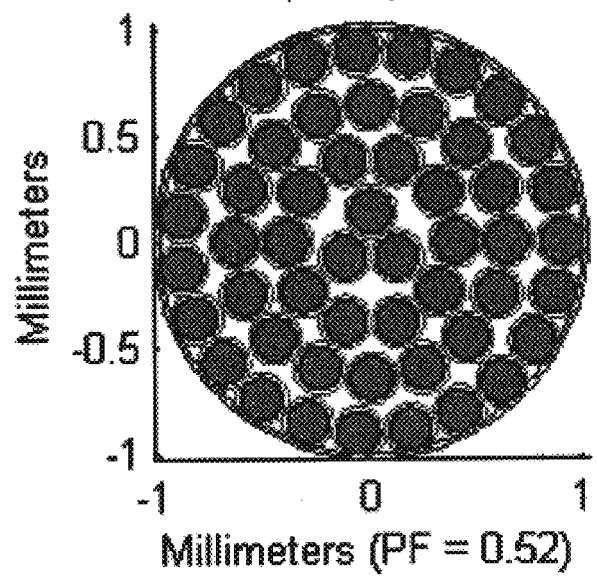
FIG. 18 is a schematic diagram illustrating an UltraSil fiber bundle termination at a detector optics termination, where a configuration of 52 fibers is shown, according to the invention.
Figure 19:
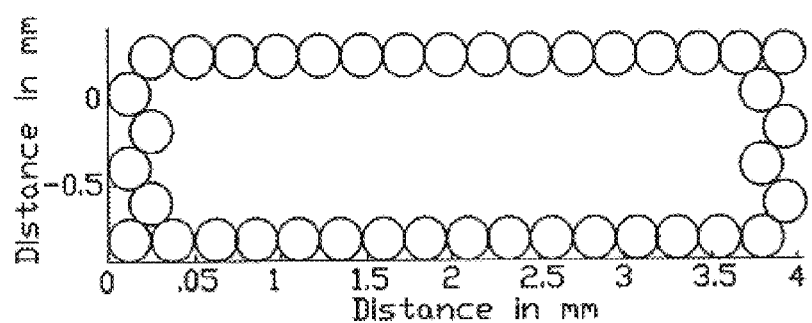
FIG. 19 is a schematic diagram illustrating a classification rectangle at skin interface (shown rotated 90 degrees) according to the invention.

The optimization of the evaluation function yields an optimal pattern. When the perimeter is incorporated that encloses a sufficient number of fibers (e.g. greater than or equal to the optimal number), and a classification fiber group is added an appropriate distance away, the result is shown in FIG. 16. This configuration contains 217 fibers in the main hex pattern (109 illumination fibers and 108 detection fibers—54 fibers of each type) and a group of 56 fibers in the classification group. Because only 105 illumination fibers are required and desirable, four of the fibers B shown in solid black are not connected to the monochromator output slit bundle termination (see FIG. 17). They are effectively dead fibers at the skin interface. Similarly, two of each detection fiber R, G shown in gray are not included in the termination at the detector optics (see FIG. 18). Four fibers in the classification bundle are not included in that particular termination (see FIG. 19). This allows for some tolerance of broken, cracked, or dead fibers after the skin interface termination of the fiber bundle is manufactured.

The following provides the specifications for the hexagonal bundle (see Table 2 below). These numbers do not include mechanical tolerances. Dimensions assume +5 $\mu$m on outer diameter of fibers to account for manufacturing variations.

Number of Illumination Fibers: 109

Number of Detection Fibers: 54 of each type (56 on the classification bundle)

Size of (mechanical) output slit of the monochromator: 4.84×1 mm

Size of the (mechanical) diameter at the detector optics: 2.0443 mm

Size of classification fiber rectangle: 3.5525×0.88153 mm

Number of Rows: 4

Number of Columns: 14

Distance from illumination hexagon to classification rectangle (center to center): 4.75 mm Dimensions of the hexagon are as follows:
  Edge length: Fiber Diameter*(9−(1−1/sqrt(3))=0.235 mm* 8.57735=2.0157 mm;
  Max Width: Fiber Diameter*(2*9−2*(1−1/sqrt(3)))= 0.235 mm* 17.1547=4.0314 mm; and
  Min Width: Edge Width*sqrt(3)=2.0157*1.732=3.4913 mm.

Number of Rows: 17

Number of Columns: 17

R, G fiber detection fiber pattern: Alternating rows with unique center row of alternating detection fibers.

TABLE 2

Target Design Goals and Fiber Specific Information, Hexagonal Bundle

| Fiber Type or Use | Number at Skin Interface | Number at Detector or Monochromator Interface | Number of Dead Fibers at Skin Interface | Fiber NA and Size w/o Buffer (Core/Clad) in $\mu$m & Fiber Name |
|---|---|---|---|---|
| Illumination Fibers | 109 | 105 | 4 (if possible, select unused fibers at corners) | 0.22 NA & 200/225* TCL-MA200H |
| Detection Fibers 1.9 $\mu$m (main) | 54 | >=52 | <=2 | 0.29 NA & 200/245* UltraSil |
| Detection Fibers 2.6 $\mu$m (main) | 54 | >=52 | <=2 | 0.29 NA & 200/245* UltraSil |
| Detection Fibers 1.9 $\mu$m (additional) | 56 | >=52 | <=4 | 0.29 NA & 200/245* UltraSil |

*+5 $\mu$m for tolerances

Alternate Design

Figure 20:
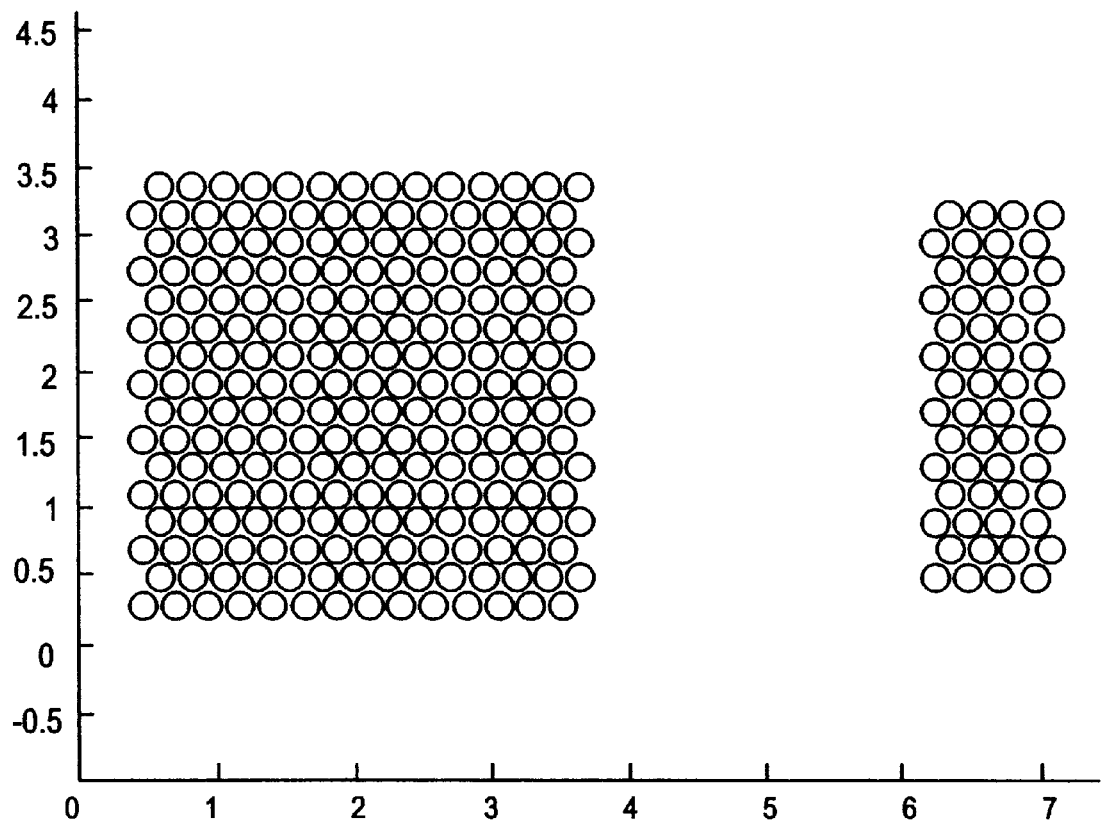
FIG. 20 is a schematic diagram illustrating a rectangular skin interface with a classification detector according to the invention.

An alternate design using the same basic pattern, only having a rectangular perimeter is now discussed (see FIG. 20). The pattern is preserved but the perimeter shape is a rectangle, not a hexagon. The aspect ratio of the rectangle is such that it is as close to a square as possible. This design represents approximately a 5% reduction in estimated results. However, it is much simpler to build because each row is the same as the other rows (all are fourteen fibers wide with an alternating pattern of detection and illumination fibers).

The following are the specifications for the rectangular bundle (see Table 3). These numbers do not include mechanical tolerances. Again, dimensions assume +5 $\mu$m on outer diameter of fibers to account for manufacturing variations.

Number of Illumination Fibers: 112

Number of Detection Fibers: 56 of each type (168 total)

Size of (mechanical) output slit of the monochromator: 4.84×1 mm

Size of the (mechanical) diameter at the detector optics: 2.0443 mm

Size of classification fiber rectangle: 3.5525×0.88153 mm

Number of Rows: 4

Number of Columns: 14

Distance from illumination hexagon to classification rectangle (center to center): 4.75 mm Size of the main detection/illumination rectangle: 3.4075×3.29 mm Number of Rows: 16

Number of Columns: 14

R, G fiber detection fiber pattern: Alternating rows with unique center row alternating detection fibers.

by a brief justification of the assumption, reason for it being ignored, or comment on why the assumption is made.

All fibers are treated as average fibers (this is especially not true at the monochromator exit slit). Because of computational considerations, it is not possible to map each fiber from the monochromator exit slit to the pattern at the skin interface and back to the detectors. Even if such a mapping did exist, it is not feasible to build the bundle in that configuration. This leads to both under- and over-estimates of the light going through any fiber. Finally, any variation in results due to this are likely overcome by variations in other parts of the system.

Extrapolation of WARF probe data is reliable. The closest separation distances (center to center) seen by the WARF probe were just over 0.5 mm. The majority of the signals in the designed probe are in fibers that are 0.25 and 0.4 mm apart. As such, this represents an extrapolation of the data from the WARF probe. The empirical model represents the light intensity detected versus illumination-to-detection distance given the light delivered to the sample by a single fiber. At close distances (<3–4 mm), where the detected signal is greatest, the error in the model is small. However, the coefficients of the model are purposely biased to represent distance configurations in which the sampled tissue volume is predominantly the dermal layer. Therefore, at greater distances, the heterogeneity of the sample and in particular the multi-layer composition of the skin causes a decrease in model accuracy. Consequently, the model appears to represent the empirical data when absorbance is dominated by the dermis, but does not accurately represent absorbance due to subcutaneous tissue.

Certain un-modeled variations are a gain which does not modify design. There are scaling factors that are not taken

TABLE 3

Target Design Goals and Fiber Specific Information, Rectangular Bundle

| Fiber Type or Use | Number at Skin Interface | Number at Detector or Monochromator Interface | Number of Dead Fibers at Skin Interface | Fiber NA and Size w/o Buffer (Core/Clad) in $\mu$m & Fiber Name |
|---|---|---|---|---|
| Illumination Fibers | 112 | 105 | 7 (if possible, select unused fibers at corners) | 0.22 NA & 200/225* TCL-MA200H |
| Detection Fibers 1.9 $\mu$m (main) | 56 | >=52 | <=4 | 0.29 NA & 200/245* UltraSil |
| Detection Fibers 2.6 $\mu$m (main) | 56 | >=52 | <=4 | 0.29 NA & 200/245* UltraSil |
| Detection Fibers 1.9 $\mu$m (additional) | 56 | >=52 | <=4 | 0.29 NA & 200/245* UltraSil |

*+5 $\mu$m for tolerances

Note that all rows are identical in that they have an illumination fiber at one end and a detection fiber at the other end. As such only one type of row needs to be made.

Discussion of Assumptions

The following is a list of the major assumptions (that are known) that are implicit in this design. Each is accompanied into account in these designs and simulations that are multiplicative in nature. Because of the nature of this problem (it is linear), these scaling factors do not change the outcome of the optimizations and therefore can be omitted.

Different sized fibers when mixed fall into a hex pack. The mixing of 225 $\mu$m diameter fibers along with 245 $\mu$m diameter fibers in a single probe would in theory, cause them to fail to fit together nicely in a hex pack. Probes that have been built do not show this to be a problem. Rather, variation in fiber separations as a result of the epoxy used and the manufacturing and assembly process yield greater tolerances. This is not a fabrication issue.

A 235 μm separation center-to-center is representative of a mixed bundle of 225 μm and 245 μm diameter fibers. For simplicity, the mean of the two fiber diameters is used to find the distances which, in turn, is used to compute the signal and noise function for a given illumination and detection pair of fibers.

The WARF probe results can be linearly scaled to represent smaller core diameter fibers. The WARF probe used 375 μm diameter fibers and the current design is using 225 and 245 μm core fibers. It is assumed that the ratio of areas ($235^2/375^2$) of the two fibers accurately represents the total signal attenuation per fiber. The diameter of the fiber core (200 μm in this case) is also a significant distance in terms of how quickly light attenuates in the skin. A new WARF probe with fibers having 200 μm cores radially distributed at 235 and 400 μm spacing is necessary to generate a more accurate noise model.

The monochromator intensity profile is not uniform across the center. This is a result of using a raytrace program to model the intensity profile. The design disclosed herein is insensitive to those variations. Rather, a more important aspect of that intensity profile is the edges, which on the raytraces are well defined. It is those edges which determine the overall range in which light can be collected from the monochromator and hence the maximum number of illumination fibers that could potentially deliver light to the skin.

The theoretical fiber packing is not similar to the simulation at the detector optics. Even with the assumption of the average packing fraction being used to determine the detector optics efficiency, the manner in which the fibers are placed into that termination is random. However, the variation is approximately a linear scaling factor, which, as already discussed, these optimizations can tolerate.

The decision to optimize for the combination band is correct. Other options are to optimize for the first or second overtone. Because of the shape of the signal-to-noise function, the design is identical if an optimization is performed for the first overtone or a combination of the first overtone and combination band. The second overtone, however, yields something different. Currently, it is believed that reading glucose occurs in either the combination band or the first overtone. If correct, the optimization decision is not of critical importance.

The absorption of fibers is ignored in these simulations. This attenuation represents a linear scaling factor, which, as already discussed, can be ignored. Additionally, the attenuation due to fiber optics is usually less than 1–2% across the entire region of interest and is of equal benefit or detriment to all designs.

Determination of an Optimal Blood Glucose Signal Representation using System Parameters Developed from a Noninvasive Tissue Model (Monte Carlo Simulation)

Summary

A number of optimization strategies were investigated to determine the best system parameter or parameters that could be used to assess different optical design arrangements quantitatively for the collection of diffuse reflectance light measured noninvasively. It was determined that the ratio of the average dermal pathlength to the average total pathlength was most suitable for the requirements of an optical design scheme. Other system parameters were considered, such as the ratio of the dermal reflectance to the total reflectance for a given radial collection distance and wavelength. However, the optimization surface was not necessarily dependent on the net analyte signal and tended to favor optical design schemes that resulted in minimal light attenuation. Slight improvements were observed when the ratio of average dermal pathlength and average total pathlength were combined but, results indicated that the system parameters still favored minimal light attenuation over net analyte signal strength.

Introduction

This approach involves the development of a strategy to assess diffuse reflectance light sampling proficiency based on a given optical interface design. System parameters such as the total pathlength, pathlength through a tissue region, penetration depth, or diffuse reflectance contributions from a particular tissue region can be used to generate a mathematical representation of the desired response (e.g. blood glucose absorption signal) for a given set of inputs. These inputs may include the radial collection distance from a source to detection arrangement, or even the depth of photon propagation into the tissue. The goal is to obtain a figure of merit, such that quantitative assessments can be made regarding the measurement system and its relation to blood glucose levels.

Methodology

The measurement of interest can be as direct as an absorption signal from a chemical constituent such as blood glucose or an intensity signal that yields an optimal configuration for light recovery and ultimately an improved net analyte signal. No matter what the measurement of interest is, a similar procedure is followed to obtain the mathematical model. Additionally, each procedure must consist of a set of criteria that governs the decision making process and how the measurement is interpreted. Several approaches to assessing the optimal values for a given optical system have been developed and explored.

Results/Discussion

Figure 21:
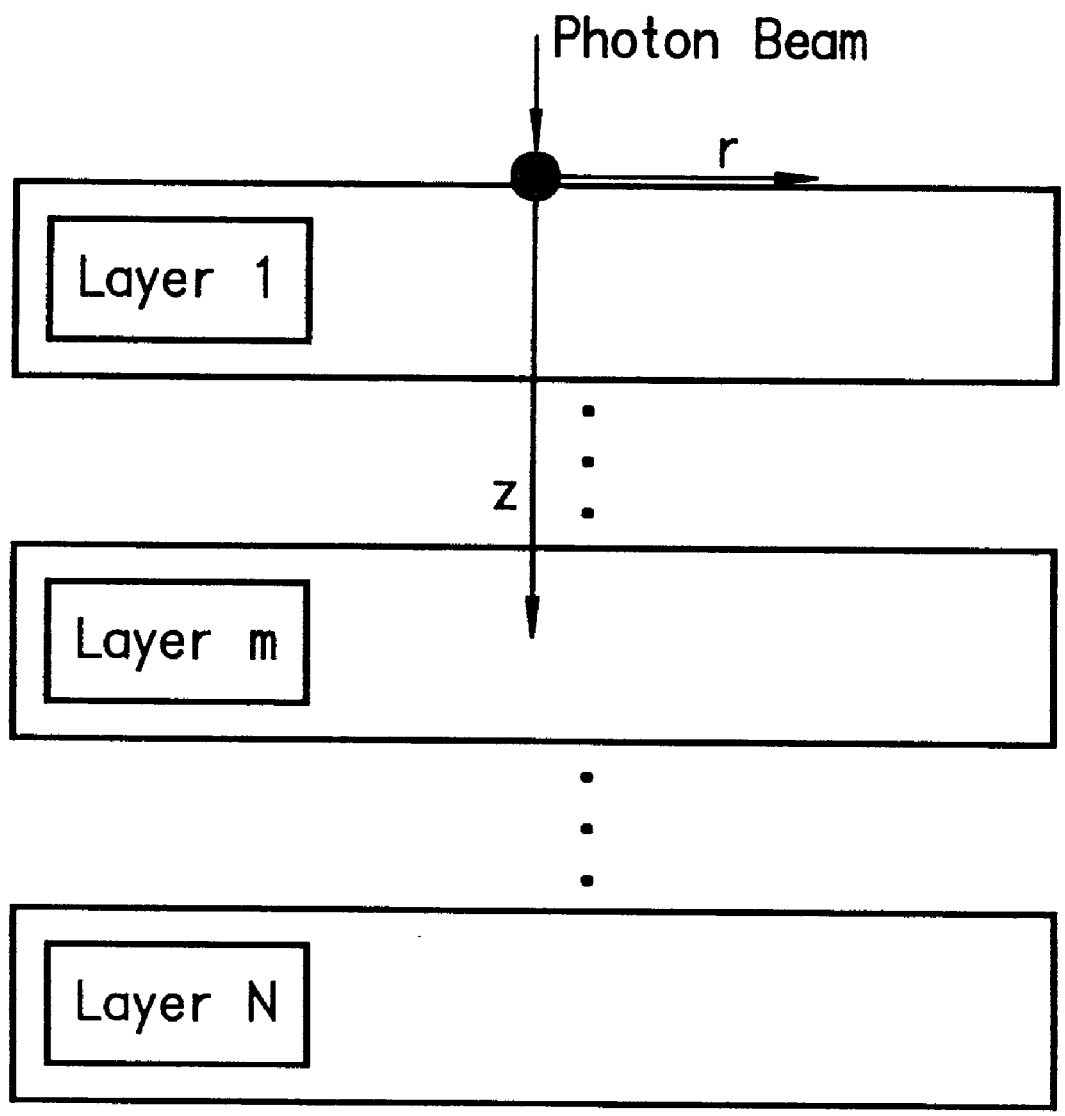
FIG. 21 is a coordinate scheme for a noninvasive tissue model.

The original optimization strategy was to use the proportion of reflectance that had penetrated to the dermal layer of the tissue model and divide that by the total amount of reflectance measured for a given radial collection distance. This procedure was then performed at every wavelength. The ratio is constrained between values of 0 and 1. The calculation of this parameter was achieved by scoring the reflectance results from a Monte Carlo simulation and then by taking the sum of the dermal reflectance contribution from a noninvasive tissue model and normalizing it with the diffuse reflectance contribution ($R_D$) at a particular radial collection distance and wavelength. This calculated as follows to yield the optimization parameter $\alpha_1$:

$$\alpha_1(r, \lambda) = \frac{\sum_{z=m}^{N} R_D(z, r, \lambda)}{R_D(r, \lambda)} \quad (8)$$

Where m is the first element of the dermal layer and N is the last element of the dermal layer as depicted in FIG. 21.

Figure 22:
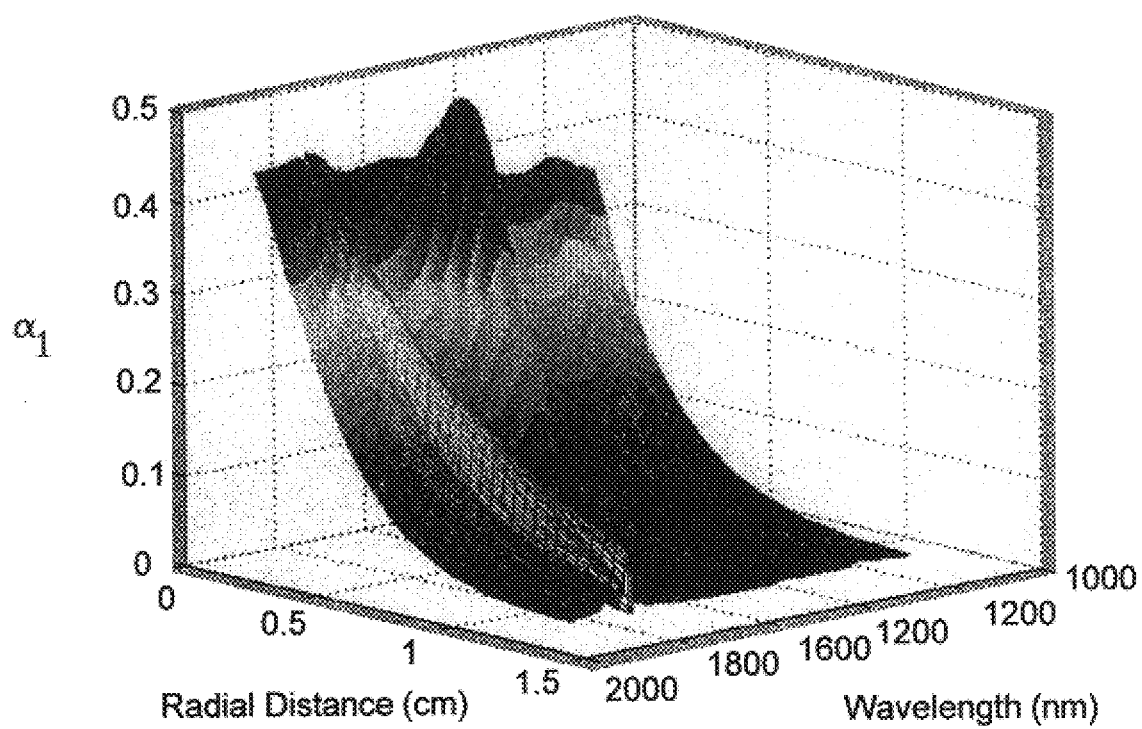
FIG. 22 is a plot showing the surface response of alpha ratio ($\alpha_1$) vs. radial collection distance and wavelength.

The rationale for this choice was based on the assumption that most of the vascularization within the tissue is contained within the dermal layers. Hence, the majority of glucose information would also be contained within these dermal layers as well. The response surface was fit to an exponential function of the form $\hat{\alpha}_1(r) = e^{(a+b \cdot r + c \cdot r^d)}$ and a plot of this function is shown in FIG. 22.

What was realized by inspecting the response surface from the first approach was that the parameter $\alpha_1$ would always favor optical designs in which the radial collection distance between the source and detector were as close as possible. This was attributed to the fact that as light propagates through the tissue its intensity decreases and hence its reflectance would also decrease. Furthermore, there is no direct relationship between the desired net analyte (glucose) signal and the $\alpha_1$ ratio.

What was proposed to compensate for this problem was the multiplication of ($\alpha_1$) the dermal reflectance ratio by the ratio of the average dermal pathlength with the average total pathlength at each radial collection distance and wavelength. The average dermal pathlength $\langle l_{Dermis}(r,\lambda) \rangle$ is the arithmetic mean of each pathlength scored in the dermal layer for a given radial collection distance and wavelength whereas, the average total pathlength $\langle l_{Total}(r,\lambda) \rangle$ is the arithmetic mean of all pathlengths measured at the same radial collection distance and wavelength. The ratio is calculated as follows:

$$\alpha_2(r, \lambda) = \alpha_1(r, \lambda) \cdot \frac{\langle l_{Dermis}(r, \lambda) \rangle}{\langle l_{Total}(r, \lambda) \rangle} \quad (9)$$

Figure 23:
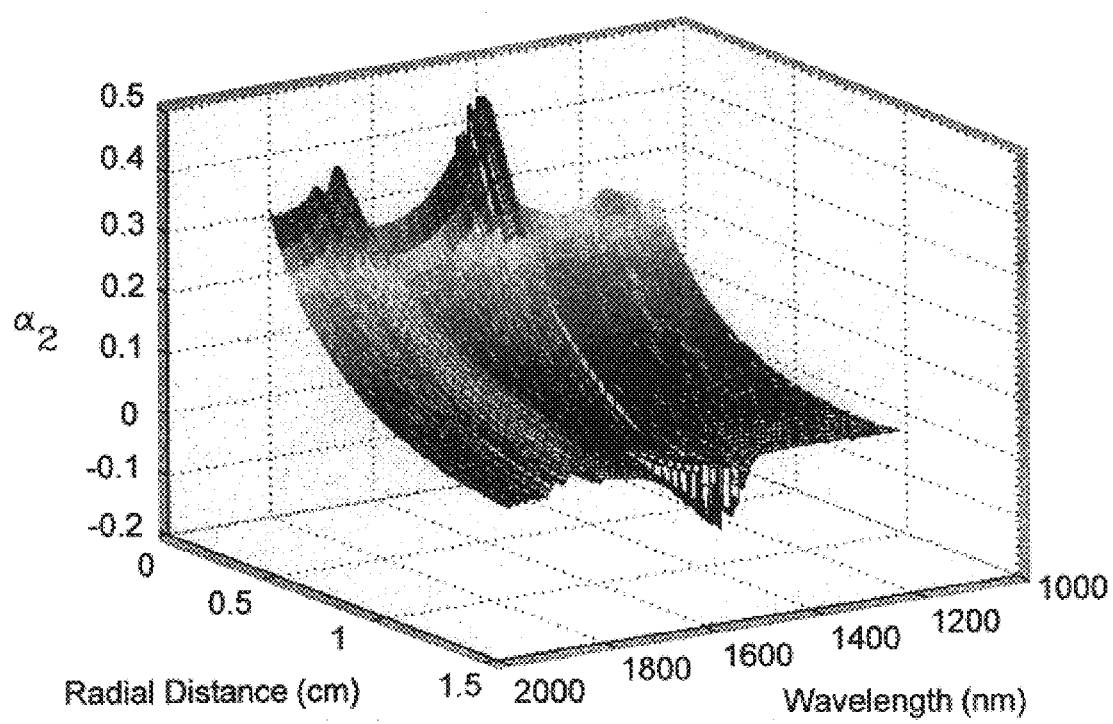
FIG. 23 is a plot showing the surface response of alpha ratio ($\alpha_2$) vs. radial collection distance and wavelength.

This ratio was chosen because it provides compensation for the decrease observed in measured sample intensities as light propagates further through the tissue. This compensation factor is reasonable because the average pathlength is proportional to the amount absorbed by the system according the Beer's Law relationship (1 A). In addition, this ratio was chosen such that $\alpha_2$ would still be constrained between the values of 0 and 1. Similarly, the surface response was fit to the following model for computational convenience $$\hat{\alpha}_2(r) = a + br + c\sqrt{r} + d\frac{\ln r}{r^2} + e\frac{1}{r^2}$$

and plotted in FIG. 23. The response surface is quite similar to that shown in FIG. 22, except that the decrease as a function of radial collection distance is not as dramatic. This is attributed to the addition of the pathlength term. Also, the model fit is not realistic at radial collection distances greater than ~1.0 cm. In addition, the characteristics of the response still favor an optical configuration that will maximize the light intensity returning from the system. This is independent of the desired signal of interest so, it is not the most desirable approach.

A more appropriate relationship that was proposed to improve the correlation with the net analyte signal was to use only the ratio of the average dermal pathlength to the average total pathlength. This has the form:

$$\alpha_3(r, \lambda) = \frac{\alpha_2(r, \lambda)}{\alpha_1(r, \lambda)} = \frac{\langle l_{Dermis}(r, \lambda) \rangle}{\langle l_{Total}(r, \lambda) \rangle} \quad (10)$$

Figure 24:
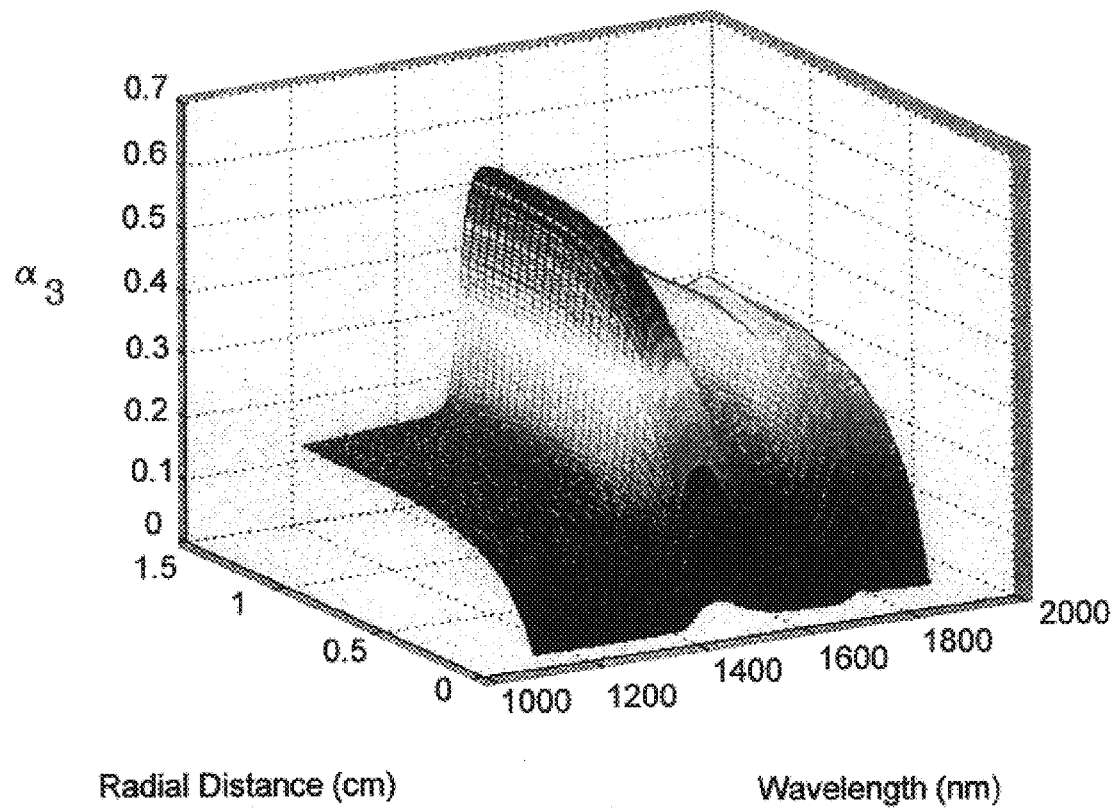
FIG. 24 is a plot showing surface response of alpha ratio ($\alpha_3$) vs. radial collection distance and wavelength.

As previously done, the surface response was fit to a model for computational convenience. This model had the form: $\hat{\alpha}_3(r) = a + br + cr^2$ and is shown in FIG. 24.

Similarly, the average dermal pathlength is calculated by taking the arithmetic mean of the individual dermal layer contributions whereas, the average total pathlength is calculated by taking the arithmetic mean of all layer contributions.

The function presented in equation (10) is a more desirable relationship because it yields a maximum value that is correlated to the net analyte signal (e.g. blood glucose signal) for a given optical design. The justification for this statement is that the net analyte signal can be viewed as the absorbance due to glucose. This is assumed to follow the Beer's Law relationship. This relationship mathematically states that the absorbance of a system is proportional to the pathlength of photon propagation through the system. Because the absorbance of the system is composed of the net analyte signal and additional contributions, the average pathlength is then proportional to the net analyte signal.

This gives a more appropriate optimization surface to utilize in the determination of preferential optical designs. One additional advantage of using equation (3) is that the results actually favor optical designs which yield a smaller average total pathlength through the system. This, in turn, slightly favors paths that yield a greater light intensity as well because, less attenuation of light is witnessed for smaller pathlengths. The physical interpretation of this is that light generally penetrates less deeply because the target system has been defined as the dermal layers. This consequence becomes an added advantage.

Recommendations

After reviewing the different strategies presented here, it is apparent that the most effective system parameter for use in the optimization of different optical design schemes is to use the ratio of the average dermal pathlength with the average total pathlength ($\alpha_3$). This most directly addresses the need for a system parameter that is proportional to the net analyte signal and includes additional features that are desirable to an overall reflectance measurement. The other system parameters presented were not directly related to the signal of interest, In this case, a blood glucose signal. However, they may still offer utility in other optical design applications in which the light intensity returning from the system is critical.

Noise Model

The noise model is the denominator of the signal-to-noise ratio that is used to evaluate and optimize fiber geometries. The requirement for the model is to provide an estimate of the noise, in absorbance units at specified wavelengths and for a particular illumination-to-detection fiber distance. The form of the developed model is given by $$N_{AO} = f(\lambda, d) = f(\cdot) \quad (11)$$

where $N_{AO}$ is the RMS noise in absorbance units, $\lambda$ is the wavelength, d is the distance between the illumination and detection fibers (for a particular fiber diameter) and $f(\cdot)$ is a nonlinear function. The structure and parameters for $f(\cdot)$ are determined empirically for each target application and measurement approach, such as the noninvasive measurement of blood glucose. In the case of a diffuse reflectance measurement of absorbance, determination of f(·) involves the propagation of the noise of the intensity measurement through the equation for calculating absorbance, A, given by $$A = -\log_{10}\left(\frac{I_S}{I_R}\right) \quad (12)$$

where $I_S$ is the measured intensity detected by a single fiber on the sample and $I_R$ is the light intensity incident upon the sample (measured with a reference standard). From the equation it is seen that the RMS noise at a particular wavelength, $N_A$, is a nonlinear function of $I_S$ and $I_R$ and the RMS noise measured with $I_S$ and $I_R$ denoted by $N_R$ and $N_S$ respectively. The expression for f(·) is found by propagating by $N_R$ and $N_s$ through the model for A and in the general case is a complex nonlinear function that includes that covariance of the noise at various wavelengths. In the preferred embodiment of the model the noise in the intensity domain is independent with respect to wavelength and is normally distributed. In this case the propagation of the noise in intensity units through Equation 12 results in $$N_A^2 = (0.4343)^2 \left[\frac{N_S^2}{I_S^2} + \frac{N_R^2}{I_R^2}\right]. \quad (13)$$

Given this equation, a model is constructed for each of the variables over all wavelengths and the various illumination to detection fiber distances by determining the individual models for $N_R$, $N_s$, $I_r$ and $I_S$ for independent variables $\lambda$ and d. While Equation 13 is applied specifically for a diffuse reflectance measurement, the approach can be applied to any for of spectroscopic measurement by propagation of noise through the equation used to calculate the analytical signal.

In Equation 13, the models for $N_S$ and $N_R$ are empirically determined for the particular instrument used to make the measurement. Further, $I_r$, is simply determined through a single measurement of the light incident on the sample. However, in the preferred embodiment the noise (in intensity units) is constant with respect to $\lambda$ and d, $N_R = N_S$ and $I_S \ll I_R$. Given these assumptions, Equation 13 is approximated by $$N_A^2 = (0.4343)^2 N_S^2 \frac{1}{I_S^2} \text{ and} \quad (14)$$

$$N_A \propto \frac{1}{I_S}. \quad (15)$$

The noise of the measurement system is inversely proportional to the intensity that is diffusely reflected off of the sample and detected. Therefore, a model needs to be constructed that returns $I_s$, for an arbitrary illumination-to-detection fiber spacing, d, and for each wavelength, $\lambda$, of interest. This model can be determined through Monte Carlo simulations (discussed above) or lumped parameter scattering models given the scattering properties of the target sample, such as the tissue. However, the preferred method is to determine the model for $I_S$ empirically through the use of a wide angle radial fiber-optic (WARF) probe as described below.

WARF Probe

A wide angle radial fiber-optic probe (WARF) was designed to provide an empirical measurement method for determining the model $$I_S = g(\lambda, d) \quad (16)$$

where $I_S$ is the light intensity detected from a single fiber at a distance, d, from the single illumination fiber and $\lambda$ is the wavelength. Further, the WARF probe is utilized to determine the optimal distance for a separate classification bundle as described below.

Figure 25:
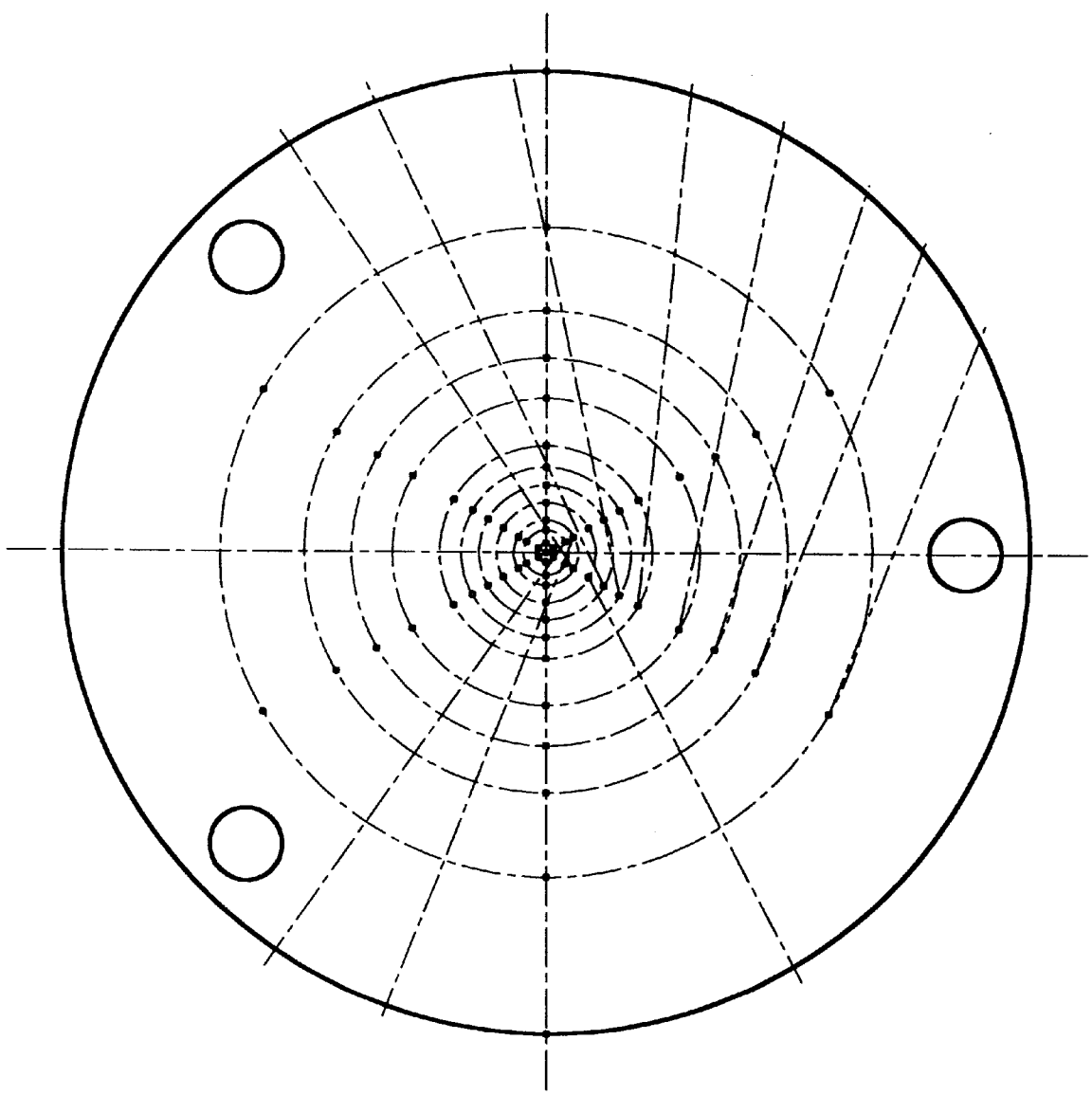
FIG. 25 is a schematic diagram showing a WARF probe that is designed with a single illumination fiber radially surrounded by sets of six detection fibers at the following illumination-to-detection distances: 0.23, 0.77, 1.3, 2.08, 2.90, 3.71, 4.70, 6.70, 8.7, 10.7, 14.7 mm.

The WARF probe, depicted in FIG. 25, was designed with a single illumination fiber radially surrounded by sets of six detection fibers at the following illumination-to-detection distances: 0.23, 0.77, 1.3, 2.08, 2.90, 3.71, 4.70, 6.70, 8.7, 10.7, 14.7 mm. While the present configuration is optimized for spectroscopic measurement of skin tissue, the invention is easily generalized to alternate illumination-to-detection distances given alternate samples. In addition, the number of detection fibers can be modified to accommodate the requirements of other samples or for coupling to any spectrometer.

In the preferred implementation, each set of six fibers are coupled to a detector of a custom designed spectrometer consisting of a quartz halogen lamp, a scanning monochromater and InGAs and extended InGAs detectors. Therefore, the WARF probe provides eleven different illumination-to-detection distances. However, one skilled in the art can appreciate that the probe can be coupled to any commercially available NIR spectrometer such as a Foss-NIRSystems Model 5000 spectrometer or a Nicolet Magna-IR 760 spectrometer.

Figure 26:
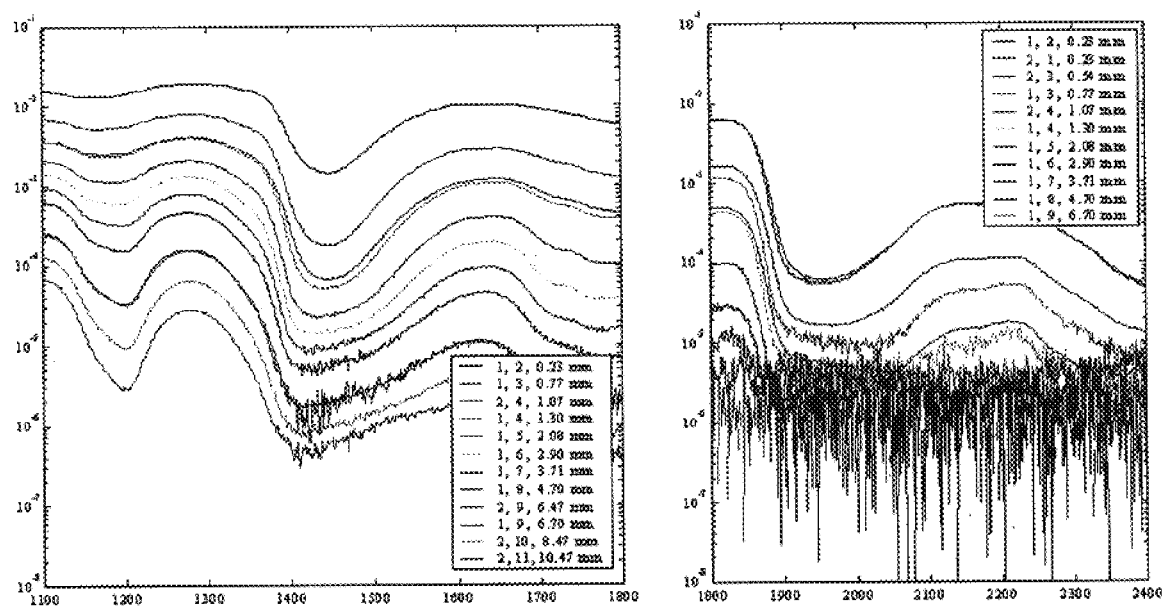
FIG. 26 is a plot showing intensity of noninvasive arm spectra vs. wavelength for various illumination-detection spacing.

An experiment was conducted with the WARF probe to provide a data set for constructing the empirical models and for fiber probe optimization. Three replicate samples at each illumination-to-detection distance of the WARF probe were collected on 10 human subjects of diverse sex, age, and body composition over the wavelength range 1050–2450 nm. In addition, to provide more information at higher light levels, the second ring of fibers found in the WARF probe were also used to illuminate the sample and the remaining fiber sets were used to detect. Particular distances were selected for analysis and the spectra were averaged over all subjects and sample replicates and normalized, and are shown in FIG. 26.

An empirical model (Equation 16) was developed to represent the detected intensity over all wavelengths and illumination-to-detection distances and is given by $$I_S e^{-(a_\lambda + b_\lambda d^{c_\lambda})} \quad (17)$$

Parameter $a_\lambda$ represents a baseline offset, $b_\lambda$ is analogous to the sum of all extinction coefficients and $c_\lambda$ provides a general method for accommodating various sample types. In the preferred embodiment the model is simplified to $$I_S = e^{-(a_\lambda + b_\lambda \sqrt{d})} \quad (18)$$

Figure 27:
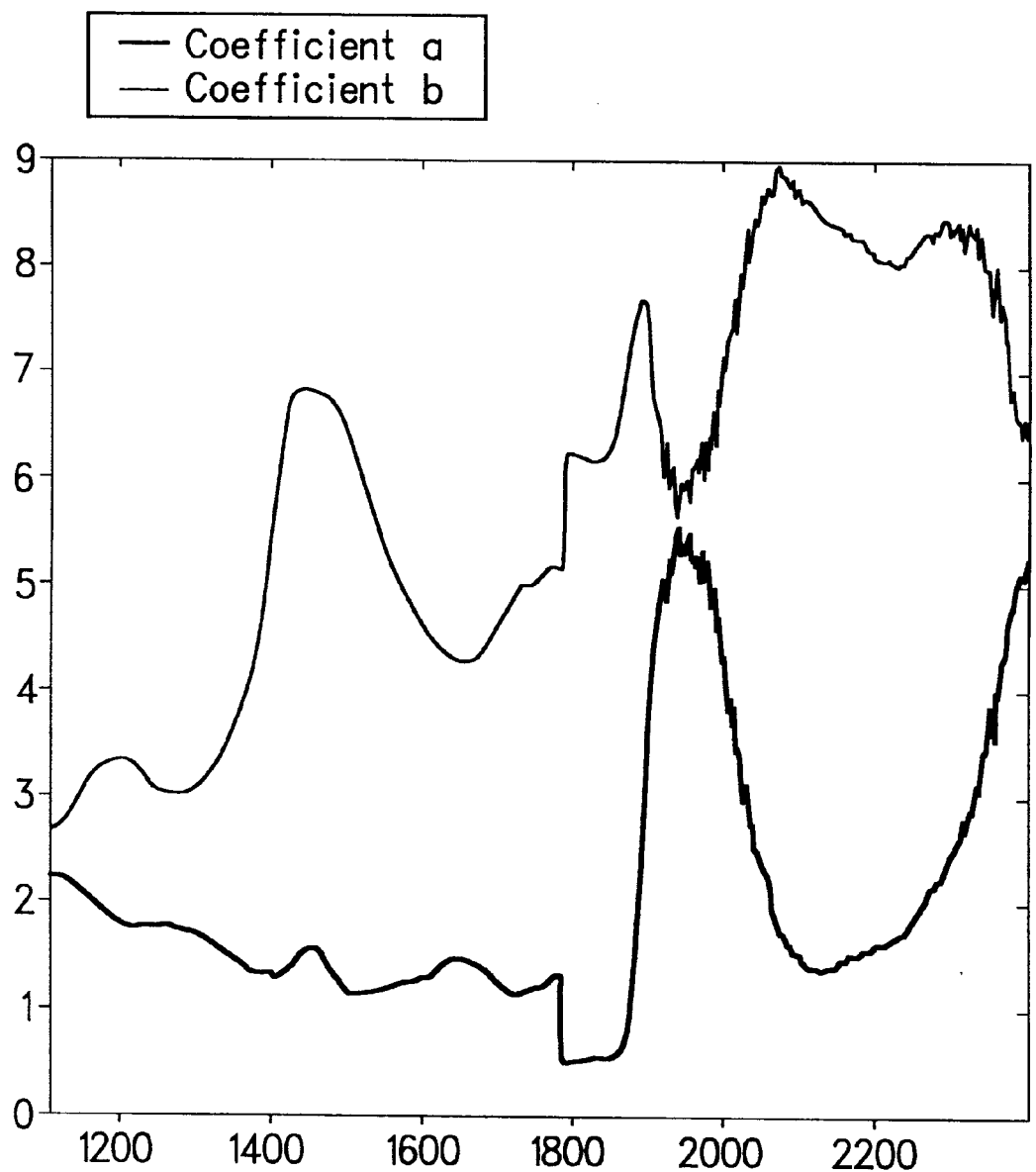
FIG. 27 is a plot showing coefficients, $a_\lambda$ and $b_\lambda$, from data collected with a WARF probe and the resulting values.

Weighted least-squares optimization was applied to determine the coefficients, $a_\lambda$ and $b_\lambda$, from data collected with the WARF probe and the resulting values are provided in FIG. 27. By this model, the absorbance (and average pathlength) increases according to the square-root of the distance between illumination and detection.

The empirical model represents the light in tensity detected versus illumination-to-detection distance given the light delivered t o the sample by a single fiber. At close distances (<3–4 mm) the error in the model is small. However, the coefficients of the model were purposely biased through the weighted least-squares calculation to represent distance configurations in which the sampled tissue volume is predominantly the dermal layer. Therefore, at greater distances, the heterogeneity of the sample and in particular the multi-layer composition of the skin, causes a decrease in model accuracy. Consequently, the model appears to represent the empirical data when absorbance is dominated by the dermis but does not accurately represent absorbance due to subcutaneous tissue. In alternate configurations the weighted least-squares method for determining the parameters is performed to optimize the accuracy of the target penetration depth.

Classification Bundle

The fiber geometry optimization procedure is performed to optimize the sampling of the target analyte signal that is located in a specific volume of the sample. However, it is often necessary to measure other characteristics or qualities of the sample that are not represented in the targeted sample volume to determine the concentration of the target analyte. For example, the need for subject classification has been demonstrated by S. Malin et al, An Intelligent System for Noninvasive Blood Analyte Prediction, supra. Such a classification may not be possible through an optimal sampling of the dermis. For example, the classification according to subject sex shown by T. Ruchti, S. Malin, J. Rennert, Classification of Individuals Based on Features Related to Sex, U.S. Provisional Patent Application Ser. No. 60/116,883, filed Jan. 22, 1999, uses the full dermis and the subcutaneous layer. Therefore, a separate bundle for classification or measurement of a property of the sample is necessary and must be designed through a separate procedure. This optimization can be accomplished through the method disclosed. However, it is desirable to use the illumination fibers from the main fiber bundle and perform only detection with the separate classification bundle. In this circumstance we provide an alternate method for determining the optimal average distance between the illumination fibers and the detection fibers of the classification bundle.

The method involves the use of the following criterion:

1. Classification performance—the spacing that provides classification performance according to the target sample characteristic or quality.
2. Noise—within the desired classification performance the distance that provides the lowest noise level in absorbance.
3. Inter-Sample Precision—within the desired classification performance the distance that is least influences by variation of the target sample.
4. Intra-Sample Precision—within the desired classification performance the distance that provides the most reproducible measurement of the target sample.

Figure 28:
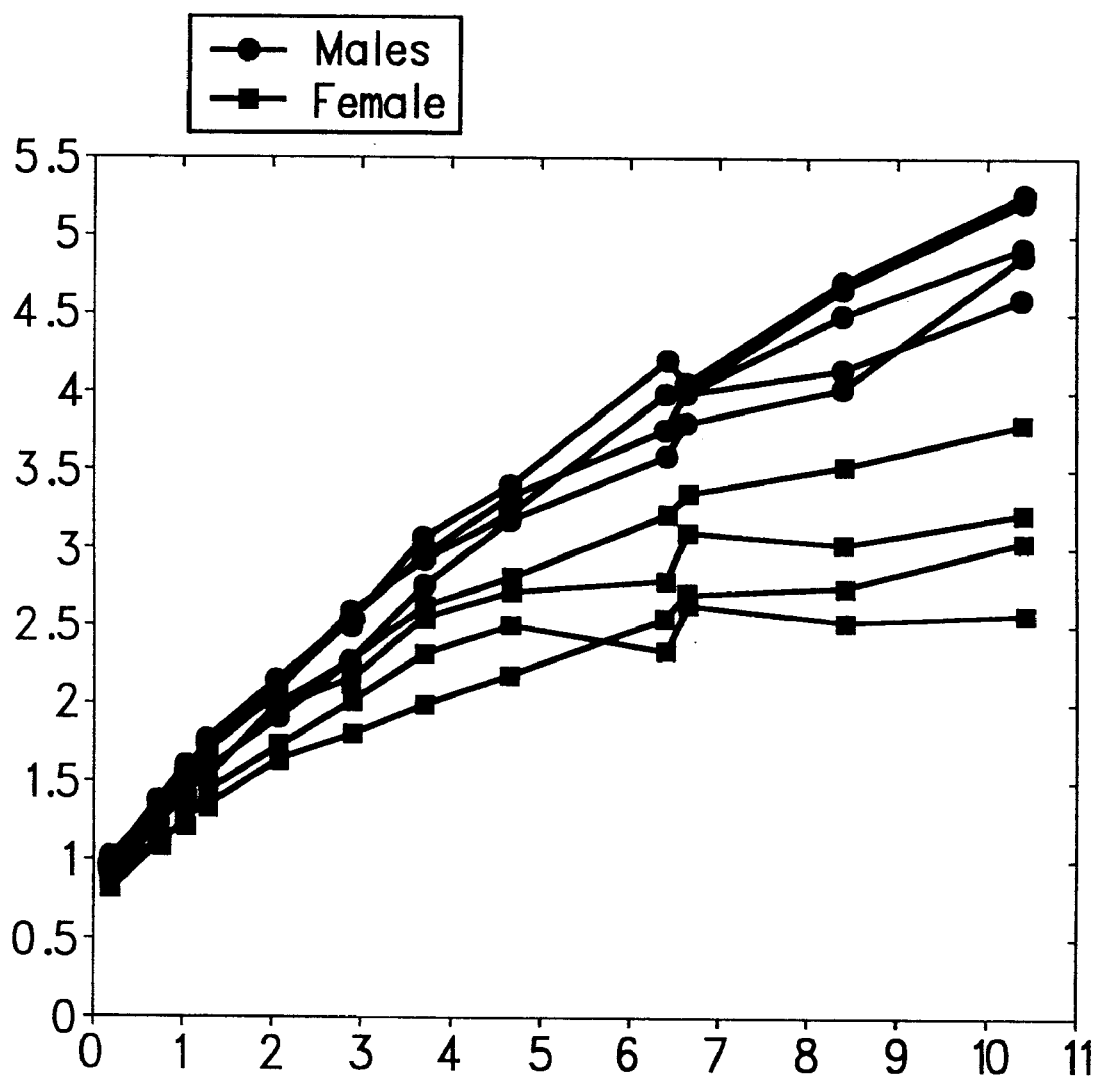
FIG. 28 is a plot showing the magnitude of water absorbance at each detection point of the WARF probe (1–10), illustrating the classification by sex that occurs as the distance from the illumination fibers increases.

In the application to the noninvasive measurement of blood analytes, the WARF probe is used to construct a data set, as described above, to perform analysis associated with each criterion. First, the water absorbance of each sample at each illumination-to-detection distance for each subject was determined as described by Ruchti et al, Classification of Individuals Based on Features Related to Sex, supra. Plots of the results are shown in FIG. 28 and demonstrate that the water absorbance feature is adequately determined for illumination-to-detection distances that are greater than 3 mm.

Figure 29:
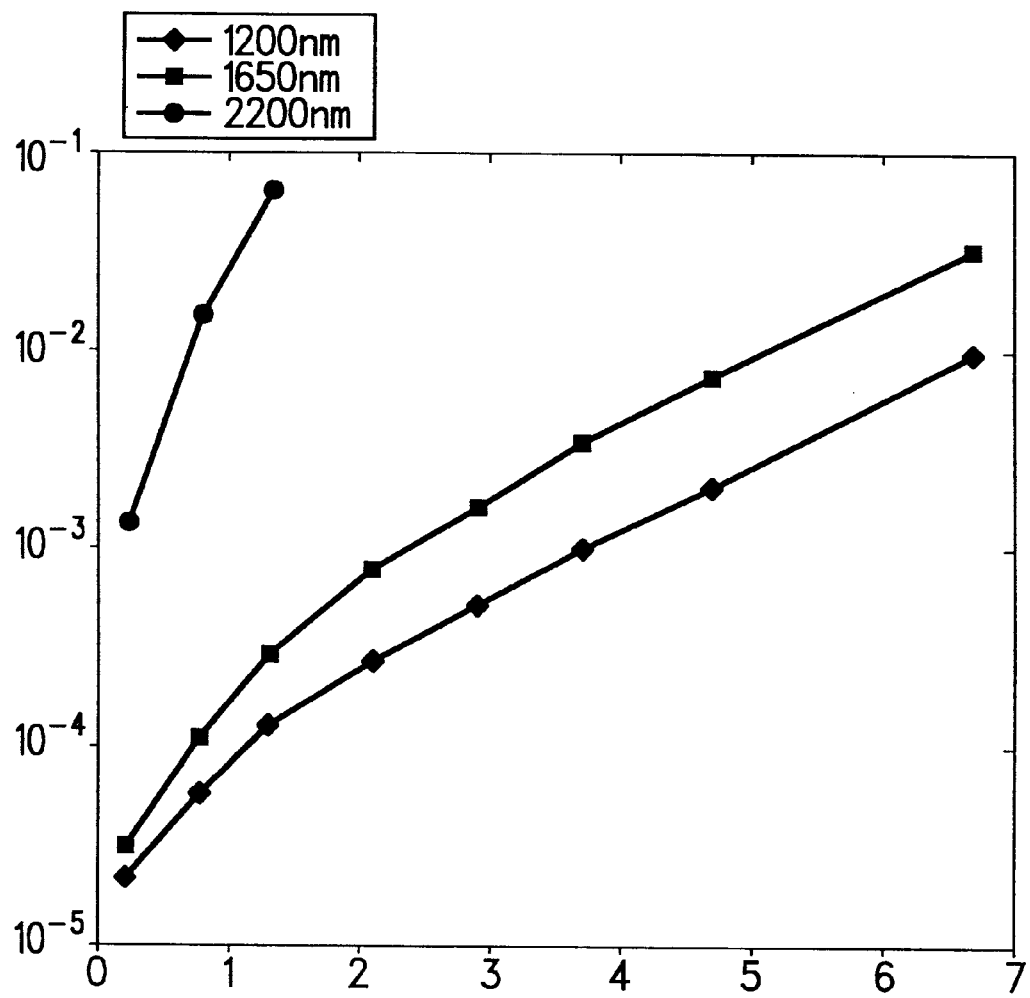
FIG. 29 is a plot showing estimated measurement noise (in absorbance units) for various illumination-to-detection distances at three separate wavelengths.

FIG. 29 shows the noise in absorbance units versus illumination-to-detection distances averaged over all subjects. From FIG. 29 it is apparent that the noise is lowest at smaller distances and therefore a distance of 3 mm is preferred.

Figure 30:
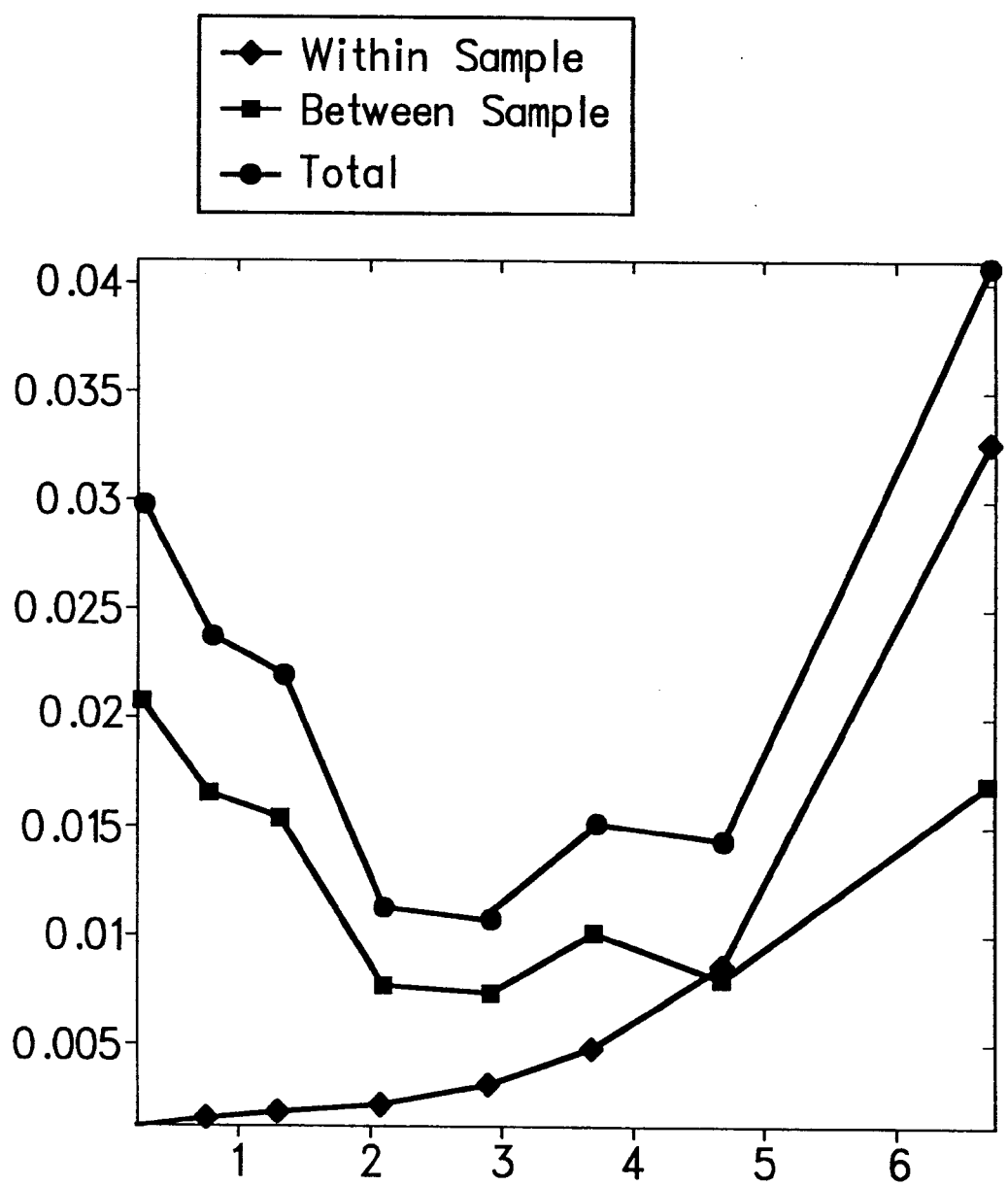
FIG. 30 is a plot showing the inter-, intra-, and total sample variation vs. illumination-to-detection distance.

FIG. 30 is a plot of the inter-sample, intra-sample and total spectral variation versus illumination-to-detection distance over all subjects. The plot shows the pooled variance within a sample, the pooled variance between samples and the total variance. From the plot of total variation 3 mm is found to be optimal in terms of measurement precision.

Therefore, it is concluded that an average illumination-to-detection distance of 3 mm is optimal for the classification bundle.

One skilled in the art can recognize that this procedure is readily applicable to other target samples with the criterion for illumination-to-detection distance relying primarily on the classification of the sample according to the target characteristic or quality.

Optimization

The method of optimization involves the configuration of the cost function, the implementation of a set of constraints and the search for a set of parameters providing the best performance. Previously we described the selection of the cost function and its configuration. Furthermore, the implementation of constraints was discussed based on mechanical considerations and available materials. The resulting unknown variables are parameters that must be determined according to the performance as reflected by the cost function. For example, unknown variables can include the fiber diameter, the quantity of fibers and the location of the fibers.

Selection of the parameters is accomplished through methods of optimization such as dynamic programming (see R. Bellman, *Dynamic Programming*, Princeton University Press, Princeton, N.J., USA (1957)), gradient search techniques (see P. Gill, W. Murray, M. Wright, *Practical Optimization*, Academic Press (1981)), random search techniques, genetic algorithms (see D. Goldberg, *Genetic Algorithm in Search, Optimization and Machine Learning*, Addison Wesley Publishing Company (1989)), or evolutionary programming (see D. Fogel, *An Introduction to Simulated Evolutionary Optimization*, IEEE Trans. On Neural Networks, vol. 5, no. 1 (January 1994)). Given a cost function and a set of parameters one skilled in the art can appreciate that any of these methods can be applied to determine an optimal or near-optimal solution.

In the preferred embodiment a genetic algorithm is employed to select from a given solution set of fibers which are used for illumination, for detection and which are not used. The method necessitates the encoding of chromosomes comprised of genes, each representing a fiber. The genes can take on the following values: 0-not used, 1-illumination fiber, 2-lower wavelength range detection fiber, 3-upper wavelength range detection fiber.

As discussed by Goldberg (see D. Goldberg, *Genetic Algorithm in Search, Optimization and Machine Learning*, supra.), the genetic algorithm is initialized with a population of possible solutions with each solution representing a different fiber geometry system. Each solution is evaluated through the cost function and assigned a performance measure. The solutions are combined (through reproduction operations) at a rate determined by their respective performance. Consequently, poorly performing solution are not selected for further use while superior configurations are combined and randomly modified. Through many iterations of this procedure a near-optimal solution is provided from a global set of possible solutions.

Conclusion

The discussion herein discloses the design process used to determine the pattern of detection and illumination optical fiber bundles for the sampling of the NIR spectrum of a subject's skin. Information about the system, specifically the monochromator output slit (to determine the optimal number of illumination fibers) and the bundle termination at the detector optics stack (to determine the optimal number of detection fibers) are both of critical importance to this design. It is those numbers that determine the ratio and number of illumination to detection fibers, significantly limiting and constraining the solution space. Additionally, information about the estimated signal and noise in the skin are essential to maximize the signal-to-noise ratio in the wavelength range of interest.

Results indicate that constraining the fibers to a hexagonal perimeter and prescribing a hex-packed pattern, such that alternating columns contain illumination and detection fibers, yields optimal results. Two detectors share the totality of the detection fibers at the sampling interface. A third group of detection fibers are used for classification purposes. In the event of any number of manufacturing issues associated with fabrication of these hexagonal bundles, a rectangular design is disclosed for implementation in place of the hexagonal design.

Although the invention is described herein with reference to the preferred embodiment, one skilled in the art will readily appreciate that other applications may be substituted for those set forth herein without departing from the spirit and scope of the present invention. Accordingly, the invention should only be limited by the Claims included below.

What is claimed is:

1. A method for optimizing fiber optic illumination and detection patterns, shapes, and locations for use in the estimation of analytes, comprising the steps of:
    systematically exploring patterns, shapes, and fiber locations to optimize an optical system design by maximizing desirable quantities in a model of said optical system; and
    estimating from said optical system model a received signal.

2. The method of claim 1, wherein said model includes signal-to-noise ratio.

3. The method of claim 2, wherein said received signal is proportional to the ratio of pathlength of an average photon in a sample to its total pathlength; and wherein said noise is approximately proportional to the intensity of said sample as a function of wavelength and detector to illumination fiber separation distance.

4. The method of claim 1, further comprising the step of:
    determining a number of fibers at a light source output and at a fiber bundle termination at a detector optics stack input;
    wherein said optimization is constrained by said light source output and said fiber bundle termination to allow a particular pattern of illumination and detection fibers to be investigated and optimized; and
    determining the shape of a perimeter of a fiber layout from said optimization.

5. The method of claim 1, further comprising the steps of:
    providing a computer program for interactive design and analysis of an arbitrary fiber layout;
    saving designs created thereby; and
    using said designs as inputs into a genetic algorithm that selects the best designs and attempts to improve upon them.

6. The method of claim 5, wherein an optimized pattern is modified as necessary to yield a regular pattern throughout and to fit said pattern into a selected external geometry.

7. The method of claim 6, wherein said external geometry is either of a hexagon or a rectangle.

8. The method of claim 1, further comprising the step of:
    providing a separate fiber optic detection field to improve subject classification.

9. The method of claim 8, wherein placement of said separate fiber optic detection field is any of:
    omitted; and
    determined through a weighted combination of any of:
        classification, performance, noise, inter-sample precision, and intra-sample precision.

10. The method of claim 1, wherein light from detector fibers is focused onto a detector.

11. The method of claim 10, wherein said detector fiber bundle is substantially the same shape as said detector to maximize the amount of light leaving the detector fibers that strikes the detector.

12. The method of claim 1, wherein light is provided by a monochromator; and wherein optical slit height for said monochromator is determined according to:

$$\text{Optical Slit Height} = (\#\text{ Rows} - 1) * \frac{\sqrt{3}}{2} * \text{Fiber Diameter} + \text{Core Diameter}.$$

13. The method of claim 2, wherein noise is modeled as sample intensity, which is a function of distance and wavelength, expressed as:

$$1/\text{Noise } e^{(a_\lambda + b_\lambda \sqrt{d})}$$

where $a_\lambda$ and $b_\lambda$ are empirically derived parameters for each wavelength, and d is the fiber separation distance.

14. The method of claim 1, further comprising the step of:
    providing an evaluation function, which is a function of wavelength, and which takes into consideration a separation in fiber distances, signal-to-noise ratio, and light source and detector optics stack characteristics.

15. The method of claim 13, wherein said evaluation function is determined for a $i^{th}$ detector as follows:

$$EF_i(\lambda) = \sum_{Illum} \sum_{Detec_i} S(\lambda, d) * \frac{1}{N(\lambda, d)} *$$

$$DP(\#Detec_i) * MP(\#Illum) * MSP(\#Illum) * SF(Type, Size),$$

where $EF_i$ is the evaluation function for the $i^{th}$ detector; the signal, S, and noise, N, are functions of wavelength, $\lambda$, and illumination to detection fiber separation distance d; DP is a detector penalty as a function of the number of detection fibers; MP is a light source penalty as a function of the number of illumination fibers; MSP is a light source size penalty as a function of the number of illumination fibers; and SF is a scaling factor that is a function of fiber sizes and types.

16. A method for optimizing fiber optic illumination and detection patterns, shapes, and locations for use in the noninvasive estimation of analytes, comprising the steps of:
    systematically exploring patterns, shapes, and fiber locations to optimize an optical system design by maximizing desirable quantities in a model of said optical system; and
    providing an evaluation function.

17. The method of claim 16, further comprising the step of:
    determining said evaluation function for a $i^{th}$ detector as follows:

$$EF_i(\lambda) = \sum_{Illum} \sum_{Detec_j} S(\lambda, d) * \frac{1}{N(\lambda, d)} *$$

$$DP(\#Detec_i) * MP(\#Illum) * MSP(\#Illum) * SF(Type, Size),$$

where $EF_i$ is the evaluation function for the $i^{th}$ detector; the signal, S, and noise, N, are functions of wavelength, $\lambda$, and illumination to detection fiber separation distance d; DP is a detector penalty as a function of the number of detection fibers; MP is a light source penalty as a function of the number of illumination fibers; MSP is a light source size penalty as a function of the number of illumination fibers; and SF is a scaling factor that is a function of fiber sizes and types.

18. The method of claim 17, further comprising the steps of:
   determining a signal-to-noise ratio for each unique fiber distance;
   multiplying said signal-to-noise ratio by a number that is equal to the number of detector/illumination fiber pairs at that distance;
   determining signal and noise once for each unique fiber distance;
   saving a value determined thereby for later use;
   pre-determining distances between all fibers; and
   using a look-up table to determine a separation distance between any two specific fibers.

19. The method of claim 17, wherein said evaluation function optimizes a design for maximum signal-to-noise ratio at a selected wavelength.

20. The method of claim 19, wherein said evaluation function is given by:

$$BestDesign_i = \max\left(\sum_{\lambda=2100\,nm}^{2250\,nm} EF_i(\lambda)\right).$$

21. A process for determining a pattern of detection and illumination optical fiber bundles for use in sampling of a subject, comprising the steps of:
   limiting and constraining a solution space by characterizing information about an illumination and sampling system to determine a ratio and number of illumination to detection fibers; and
   estimating signal and noise at a location where said subject is sampled to maximize the signal-to-noise ratio in a wavelength range of interest.

22. The method of claim 21, wherein illumination is provided by a monochromator; and wherein a monochromator output slit is characterized to determine an optimal number of illumination fibers.

23. The method of claim 21, wherein detection is provided by a bundle termination at a detector optics stack; and wherein said detector optics stack is characterized to determine an optimal number of detection fibers.

24. A detection and illumination optical fiber bundle for sampling of a subject, comprising:
   a plurality of optical fibers constrained to either of a hexagonal or a rectangular perimeter and prescribing a hex-packed pattern, wherein alternating columns contain illumination and detection fibers, and wherein two detectors share the totality of detection fibers at a sampling interface.

25. The fiber optic bundle of claim 24, further comprising:
   a separate group of detection fibers used for classification purposes.

26. The fiber optic bundle of claim 24, wherein fibers are positioned such that each end of a bundle center fiber is centered at an opposing end of the bundle; and
   wherein each end of each and every other fiber in the bundle has a position at one end of said bundle that corresponds to position of said fiber's opposing end at the opposing end of said bundle.

27. The fiber optic bundle of claim 24, wherein said detection and illumination fibers have the same characteristics.

28. The fiber optic bundle of claim 27, wherein said fiber characteristics comprise any of type, size, numeric aperture, and core-to-clad ratio.

29. The fiber optic bundle of claim 25, wherein placement of said separate fiber optic detection field is any of:
   omitted; and
   determined through a weighted combination of any of;
      classifications performance, noise, inter-sample precision, and intra-sample precision.

30. A computer readable medium upon which a computer program is stored, said computer program capable of instructing a computer to implement a method for optimizing fiber optic illumination and detection patterns, shapes, and locations for use in estimation of analytes, said method comprising the steps of:
   systematically exploring patterns, shapes, and fiber locations to optimize an optical system design by maximizing desirable quantities in a model of said optical system; and
   estimating from said optical system model a received signal.

* * * * *